(12) United States Patent
Rhee et al.

(10) Patent No.: US 6,638,735 B1
(45) Date of Patent: Oct. 28, 2003

(54) PLASMID FOR GENE EXPRESSION IN PICHIA CIFERRII AND TRANSFORMATION METHOD USING THE SAME

(75) Inventors: Sang Ki Rhee, Seoul (KR); Jung Hoon Bae, Taejon (KR); Eui Sung Choi, Taejon (KR); Jung Hoon Sohn, Taejon (KR); Hyun Ah Kang, Taejon (KR); Chang Seo Park, Kwachun (KR)

(73) Assignees: Doosan Corporation, Kyungki-Do (KR); Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/674,826

(22) PCT Filed: Oct. 31, 1998

(86) PCT No.: PCT/KR98/00346

§ 371 (c)(1),
(2), (4) Date: Jul. 17, 2001

(87) PCT Pub. No.: WO99/57279

PCT Pub. Date: Nov. 11, 1999

(30) Foreign Application Priority Data

May 7, 1998 (KR) ......................................... 1998/16309
May 7, 1998 (KR) ......................................... 1998/16310
Aug. 21, 1998 (KR) ......................................... 1998/33969

(51) Int. Cl.[7] .......................... C12P 21/06; C12N 15/00; C12N 15/87; C12N 1/14; C07H 21/04
(52) U.S. Cl. .................. 435/69.1; 435/320.1; 435/461; 435/254.23; 435/255.5; 435/255.6; 536/23.1; 536/23.2
(58) Field of Search ............................ 435/320.1, 69.1, 435/70.1, 71.1, 455, 461, 254.23, 255.51, 255.6; 536/23.11, 23.7, 23.21, 24.2, 23.2

(56) References Cited

U.S. PATENT DOCUMENTS

| | | | |
|---|---|---|---|
| 4,851,350 A | 7/1989 | Stevens, Jr. et al. | 435/262 |
| 5,068,187 A | 11/1991 | Takeichi et al. | 435/106 |
| 5,618,706 A | 4/1997 | Casey et al. | 435/128 |
| 5,849,524 A | * 12/1998 | Kondo et al. | 435/69.1 |

FOREIGN PATENT DOCUMENTS

| | | |
|---|---|---|
| EP | 0 300 287 B1 | 1/1989 |
| EP | 0 688 871 A2 | 12/1995 |
| WO | WO 94/10131 | 5/1994 |

OTHER PUBLICATIONS

Ngo et al. Computational complexity, protein structure prediction, and the Levinthal paradox. In: The protein folding problem and tertiary structure prediction (Merz et al., eds.), Birkhauser, Boston, pp. 491–495, 1994.*

Rudinger, J. Characteristics of the amino acids as components of a peptide hormone sequence. In: Peptide hormones (Parsons, J.A., ed.), University Park Press, Baltimore, pp. 1–7, 1976.*

Yechezkel Barenholz, Nathan Godot, Eliyahu Valk, Shimon Gatt, Identification of the enzymatic lesion responsible for the accumulation of acetylated sphingosine bases in the yeast *Hansenula ciferr*, Biochimica et Biophysica Acta, 306, pp. 341–345, (1973).

Lynfred J. Wickerham and Frank H. Stodola; Formation Of Extracellular Sphingolipides By Microorganisms; J. Bacteriol., vol. 80, pp. 484–491, (1960).

Yuzo Yamad, Kojiro Maeda, and Kozaburo Mikata: The Phylogenetic Relationships of the Hat–shaped Ascospore–forming, Nitrate–assimilating *Pichia* Species, Formerly Classified in the Genus *Hansenula* SYDOW et SYDOW, Based on the Partial Sequences of 18S and 26S Ribosomal RNAs (Isaccharomycetaceae): The Proposals of Three New Genera, Ogataea, Kuraishia, and Nakazawae: Biosci; Biotech. Biochem., 58(7), pp. 1245–1257, (1994).

Keiji Kondo, Toshiko Saito, Susmu Kajiwara, Masamichi Takagi, Norihiko Misawa, A Transformation System for the Yeast *Candida utilis*: Use of a Modified Endogenous Ribosomal Protein Gene as a Drug–Resistant Marker and Ribosomal DNA as an Integration Target for Vector DNA, Journal of Bacteriology, vol. 177, pp. 7171–7177, (1995).

Klass Nico Faber, Peter Haima, Wim Harder, Marten Veenhuis, Geert AB, Highly–efficient electrotransformation of the yeast *Hansenula polymorpha*, Curr. Genet., 25, pp. 305–310 (1994).

M. Marek Nagiec, Julie A. Baltisberger, Gerald B. Wells, Robert L. Lester, and C. Dickson, The *LCB2* gene of *Saccharomyces* and the related *LCB1*gene encode subunits of serine palmitoyltransferase, the initial enzyme in sphingolipides synthesis, Proc. Natl. Acad. Sci. USA, vol. 91, pp. 7899–7902, (1994).

M. Marek Nagiec, Robert L. Lester, Robert C. Dickson, Sphingolipid synthesis: identification and Characterization of mammalian cDNAs encoding the Lcb2 subunit of serine palmitoyltransferase, Gene, 177, pp. 237–241 (1996).

(List continued on next page.)

Primary Examiner—James Ketter
Assistant Examiner—Quang Nguyen
(74) Attorney, Agent, or Firm—Nixon & Vanderhye

(57) ABSTRACT

Expression cassettes for transforming *Pichia ciferrii* and their use are disclosed. The present invention relates to expression cassettes containing *Pichia ciferrii* ribosomal DNA fragment, CYH[r] gene resistant to cycloheximide, and a desired gene. Expression cassette further comprising *Pichia ciferrii* GAPDH promoter gene which allows an increase in the expression of the desired gene also provided. Moreover, the present invention provides a process for producing tetraacetyl phytosphingosine using transformed *Pichia ciferrii* cells with the expression cassettes in a higher yield.

18 Claims, 7 Drawing Sheets

OTHER PUBLICATIONS

Kentaro Handa, Tomoko Hara, Masahiro Nishijima, Osamu Kuge, Robert C. Dickson, and M. Marek Nagiec, A Mammalian Homolog of the Yeast *LCB1* Encodes a Component of Serine Palmitoyltransferase, the Enzyme Catalyzing the First Step in Sphingolipid Synthesis, vol. 272, No 51, pp. 32108–32114, (1997).

Bertram Weiss and Wilhelm Stoffel, Human and murine serine–palmitoy–CoA transferase Cloning, expression and characterization of the key enzyme in sphingolipid synthesis, Eur. J. Biochem., 249, pp. 239–247 (1997).

Peter J. Kniskern, Arpi Hagopian, Donna L. Montgomery, Pamela Burke, Nancy R. Dunn, Kathryn J. Hofmann, William J. Miller and Ronald W. Ellis, Unusually high–level expression of a foreign gene (hepatitis B virus core antigen) in *Saccharomyces cerevisiae*, Gene, 46, pp. 135–141 (1986).

James Travis, Maurice Owen, Peter George, Robin Carrell, Steven Rosenberg, Robert A. Hallewell, and Philip J. Barr, Isolation and Properties of Recombinant DNA Produced Variants of Human $\alpha_1$–Protease Inhibitor, The Journal of Biological Chemistry, vol. 260, No. 7, pp. 4389–4389, (1995).

Robert A. Hallewell, Robert Mills, Patricia Tekamp–Olson, Russel Blancher, Steven Rosenberg, Fritz Otting, Frank R. Masiarz, Carl J. Scandella, Amino Terminal Acetylation of Authentic Human Cu,Zn Superoxide Dismutase Produced in Yeast, Bio/tech., vol. 5, pp. 363–366, (1987).

Steven Rosenberg, Doris Coit, and Patricia Tekamp–Olson, Glyceraldehyde–3–phosphate Dehydrogenase–Derived Expression Cassettes for Constitutive Synthesis of Heterologous Proteins, Methods in Enzymology, vol. 185, pp. 341–351, (1990).

Hans R. Waterham, Mary Ellen Digan, Patricia J. Koutz, Stephen V. Lair, James M. Cregg, Isolation of the *Pichia pastoris* glyceraldehydes–3–phosphate dehydrogenase gene and regulation and use of its promoter, Gene, 186, pp. 37–44, (1997).

John R. Johnston, Yeast genetics, molecular aspects, IRL press, pp. 107–123, (1988).

Yechezkel Barenholz, Irit Edelman and Shimon Gatt, The Metabolic Basis For The Accumulation Of Acetylated Sphingosine Basis In the Yeast *Hansenula Ciferri*, Biochema et Biophysica Acta, 248, 458–465, (1971).

* cited by examiner

PLASMID FOR GENE EXPRESSION IN PICHIA CIFERRII AND TRANSFORMATION METHOD USING THE SAME

BACKGROUND OF THE INVENTION

1. Field of the Invention

The present invention relates to expression cassettes for transforming *Pichia ciferrii*. More particularly, it relates to expression cassettes containing *Pichia ciferrii* ribosomal DNA fragment, CYH$^r$ gene resistant to cycloheximide, and a desired gene, and to uses thereof.

2. Description of the Prior Art

*Pichia ciferrii* has been used to biologically desulfurize coals (Stevens et al., U.S. Pat. No. 4,851,350), to produce D-alpha-amino acids (Takelchi et al., U.S. Pat. No. 5,068,187), to produce (S)-1-phenyl-1,3-propandiol (Ajinomoto, JP 6-90789A) or to produce secondary alcohols by stereospecific ketone reduction (Merck, EP-300287). Further, it produces and secretes tetraacetyl phytosphingosine (TAPS) which is a precursor of ceramides (Barenholz et al., Biochem. Biophys. Acta, 248, 458, 1971; ibid, 306, 341, 1973).

Phytosphingosines including TAPS, like ceramides, show an activity of surface skin-protection and of preventing excessive water-loss and dry out of the skin, facilitating their uses in cosmetics. They can be obtained from various microorganisms and easily converted to ceramides by N-acylation.

TAPS productions by wild type *Pichia ciferrii* ATCC 14091 and F-60-10 (NRRL 1301) are not satisfactory for commercial uses. To improve the production of TAPS in the strains of *Pichia ciferrii*, attempts to provide mutants which are capable of producing a higher level of TAPS have been made (Wickerham & Burton, J. Bacteriol., 80, 484, 1960; U.S. Pat. No. 5,618,706). The present inventors also developed novel useful mutant (KFCC-10937) which allows a larger amount of TAPS production in a shorter time (KR 98-49305A).

*Pichia ciferrii* had been classified into genus Hansenula and is recently reclassified into genus Pichia by 5S-RNA analysis (Yamada et al., Biosci, Biotechnol. Biochem., 58, 1245, 1994). By this reason, the genetic study of the Pichia yeasts is not sufficient and transformation method of *Pichia ciferrii* has not been established.

The present invention provides plasmid prACL2 comprising *Pichia ciferrii* serine palmitoyl transferase gene and a transformed *Pichia ciferrii* cell which allows an improved production of TAPS.

The inventors found that the known transformation method for *Candida utilis* (Kondo et al., J. Bacteriol., 177, 7171, 1995) can be modified and applied to the *Pichia ciferrii*. They cloned *Pichia ciferrii* ribosomal protein L41-coding gene to determine its nucleotide sequence and manipulated to give a resistance to cycloheximide, an antibiotic from yeasts, so as to be used as a selection marker. Thus recombinant gene may be linked to a plasmid which carry a desired gene to give an expression cassette which is useful to transform *Pichia ciferrii* in which the desired gene is expressed.

Moreover, the inventors succeeded in cloning of *Pichia ciferrii* GAPDH promoter gene and found that its insertion into the expression cassette allows an unexpected improvement of the expression level. In fact, they increased the production amount of TAPS by transforming the strain of *Pichia ciferrii* with the expression cassette carrying LCB2 gene as a desired gene and culturing the resulting transformed cells. LCB2 gene codes for palmitoyl transferase which is involved in the TAPS synthesis in the living body.

SUMMARY OF THE INVENTION

Accordingly, an object of the present invention is to determine and use genetic information of *Pichia ciferrii* ribosomal protein L41 gene.

Another object of the present invention is to provide an expression cassette for transforming *Pichia ciferrii*, which comprises *Pichia ciferrii* ribosomal DNA, *Pichia ciferrii* L41 gene as a selection marker, and a desired gene. In one preferred embodiment of the present invention, the marker is a gene conferring resistance to an antibiotic cycloheximide.

Another object of the present invention is to provide a method for transforming *Pichia ciferrii* with a plasmid containing the expression cassette.

The present invention determines and uses genetic information of *Pichia ciferrii* glyceraldehyde-3-phosphate dehydrogenase (GAPDH) gene and GAPDH promoter gene.

The present invention provides an expression cassette for transforming *Pichia ciferrii*, which comprises *Pichia ciferrii* ribosomal DNA, *Pichia ciferrii* L41 gene as a selection marker, *Pichia ciferrii* GAPDH promoter gene and a desired gene. In one preferred embodiment of the present invention, the marker is a gene conferring resistance to an antibiotic cycloheximide.

The present invention further provides an expression cassette for transforming *Pichia ciferrii*, which comprises *Pichia ciferrii* ribosomal DNA, *Pichia ciferrii* L41 gene as a selection marker, *Pichia ciferrii* GAPDH promoter gene, a desired gene and *Pichia ciferrii* ribosomal DNA. In one preferred embodiment of the present invention, the marker is a gene conferring resistance to an antibiotic cycloheximide.

The present invention determines and uses genetic information of *Pichia ciferrii* serine palmitoyl transferase which is involved in TAPS synthesis.

The present invention provides plasmid prACL2 comprising an expression cassette having *Pichia ciferrii* serine palmitoyl transferase gene and a transformed *Pichia ciferrii* cell with an improved production of TAPS.

The present invention further provides plasmid prACGL2 comprising an expression cassette having *Pichia ciferrii* serine palmitoyl transferase gene and a *Pichia ciferrii* transformant with an improved production of TAPS.

The present invention further provides plasmid prHECGL2 comprising an expression cassette having *Pichia ciferrii* serine palmitoyl transferase gene and a *Pichia ciferrii* transformant with an improved production of TAPS.

The present invention still further provides a method for producing TAPS by culturing the transformed *Pichia ciferrii* cells.

The objects mentioned above, other features and applications of the present invention would be much more apparent by those of ordinary skills in the art from the following explanation in detail.

restriction enzymes in bold letters indicate the enzymes used for linearization of the respective plasmids;

arrows indicate the transcription direction of the genes; and plasmid prACL2 carries LCB2 gene coding for serine palmitoyl transferase from *Pichia ciferrii*.

Figure 2:
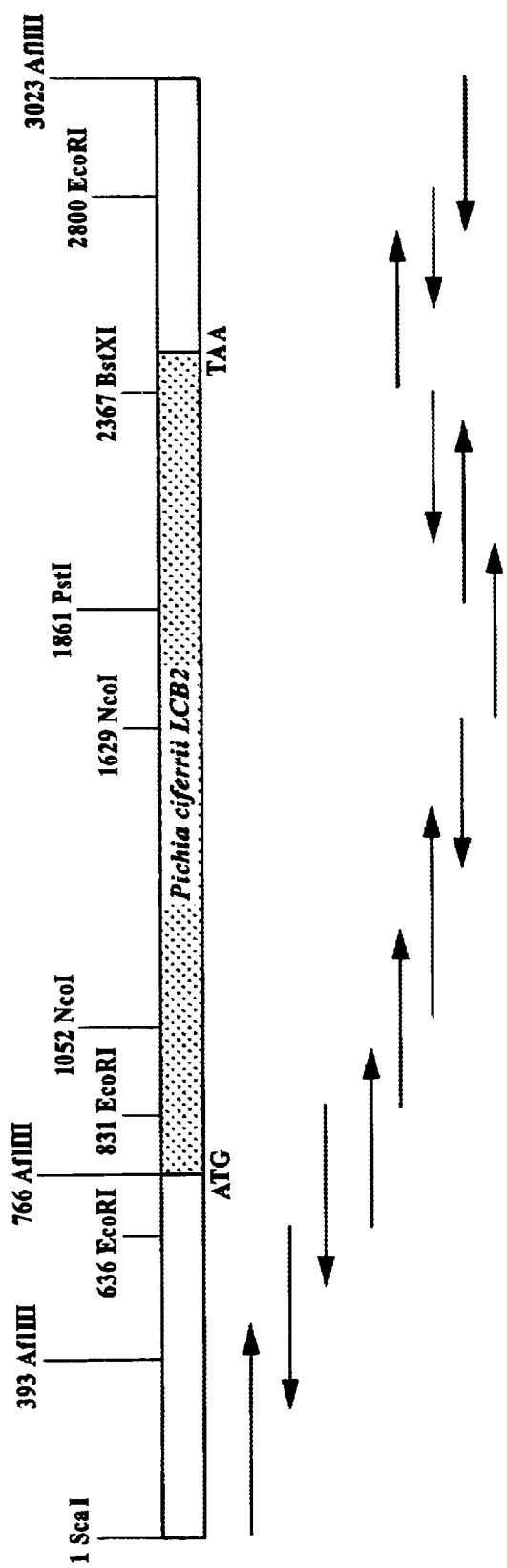

FIG. 2 is a restriction map of *Pichia ciferrii* LCB2 gene, and the orientation and the length of the arrows indicate the direction and degree of nucleotide sequencing, respectively.

Figure 3:
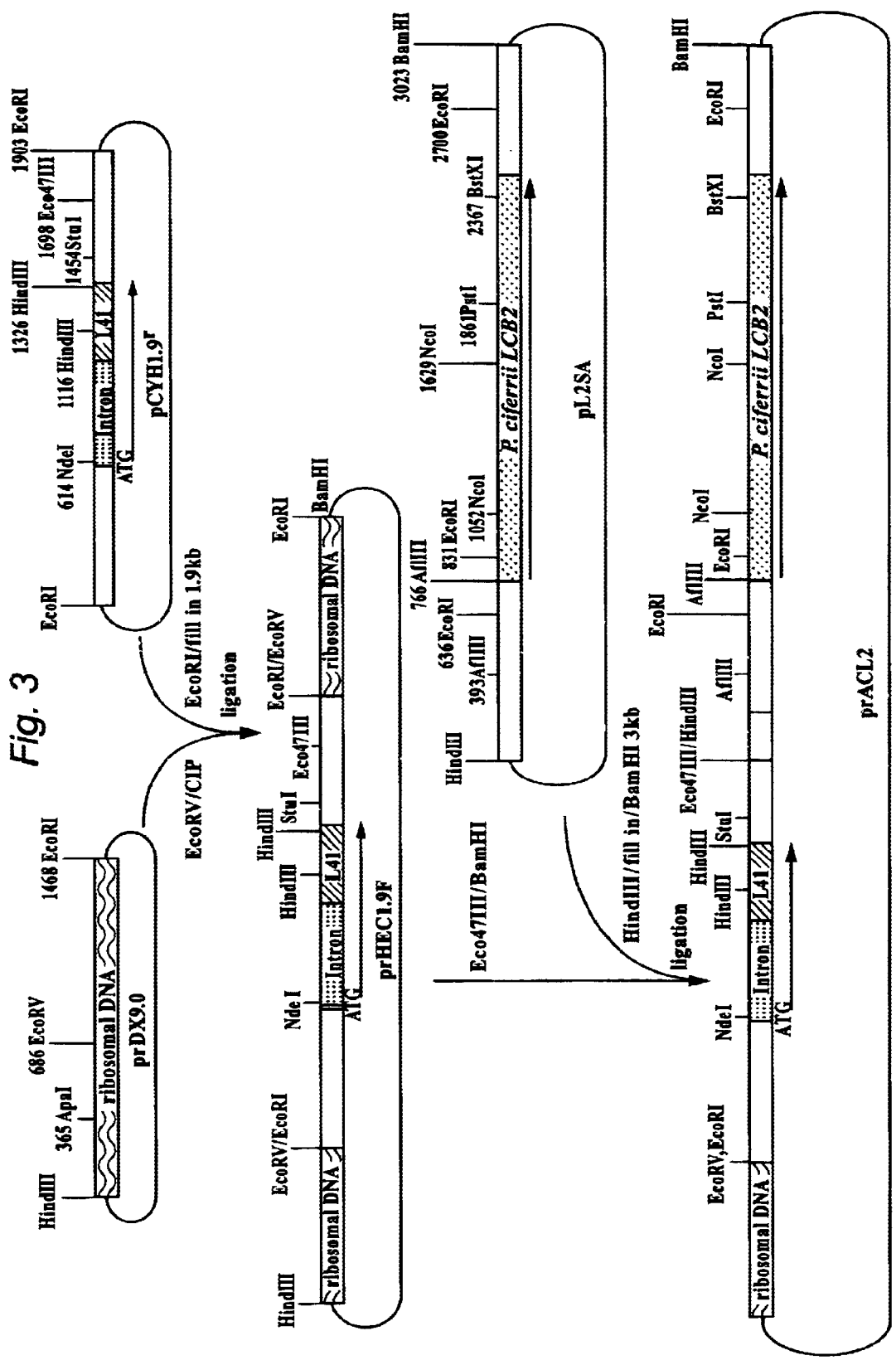

FIG. 3 represents the construction and restriction map of plasmid prACL2.

Figure 4:
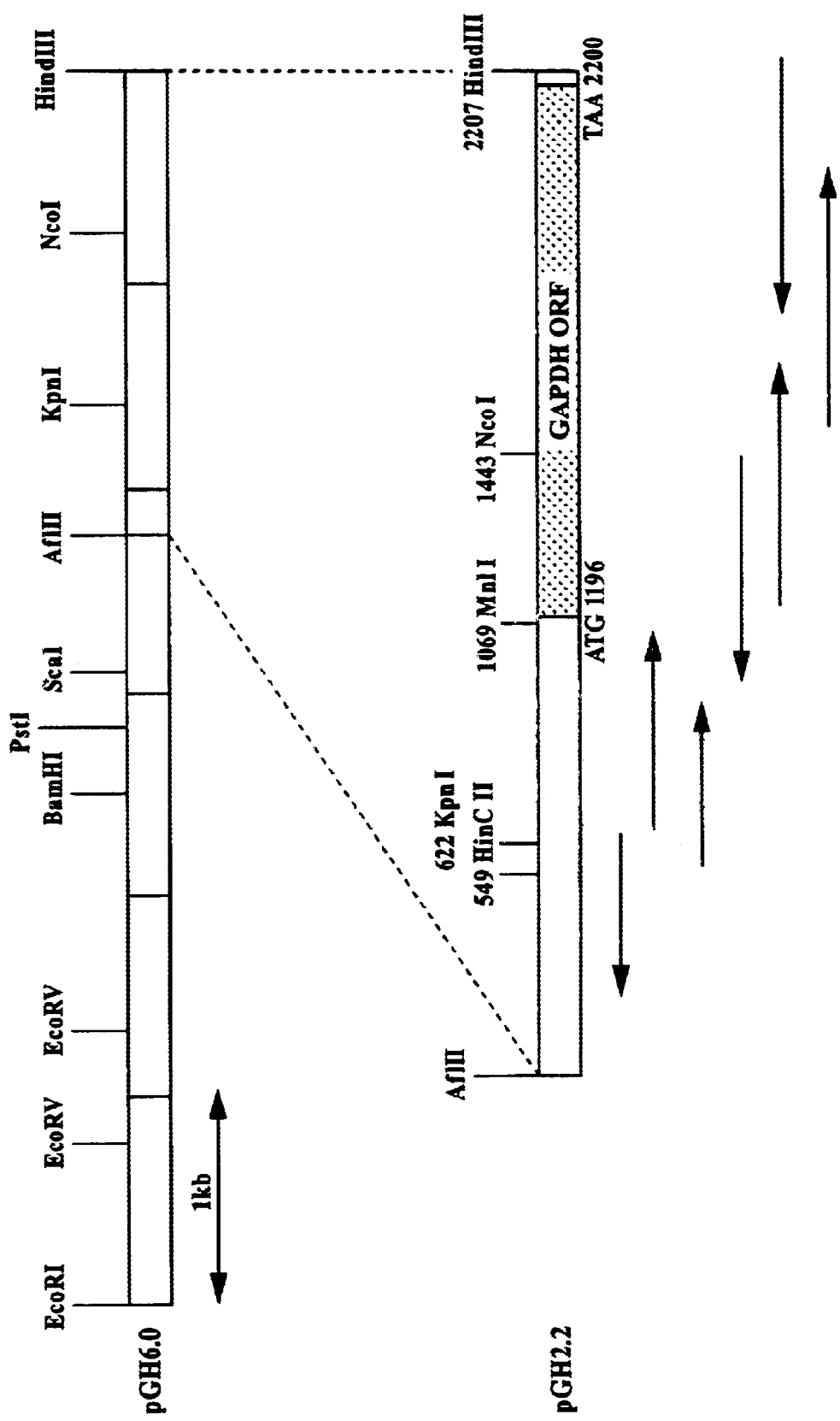

FIG. 4 is a restriction map of *Pichia ciferrii* GAPDH gene, and the orientation and the length of the arrows indicate the direction and degree of nucleotide sequencing, respectively.

Figure 5:
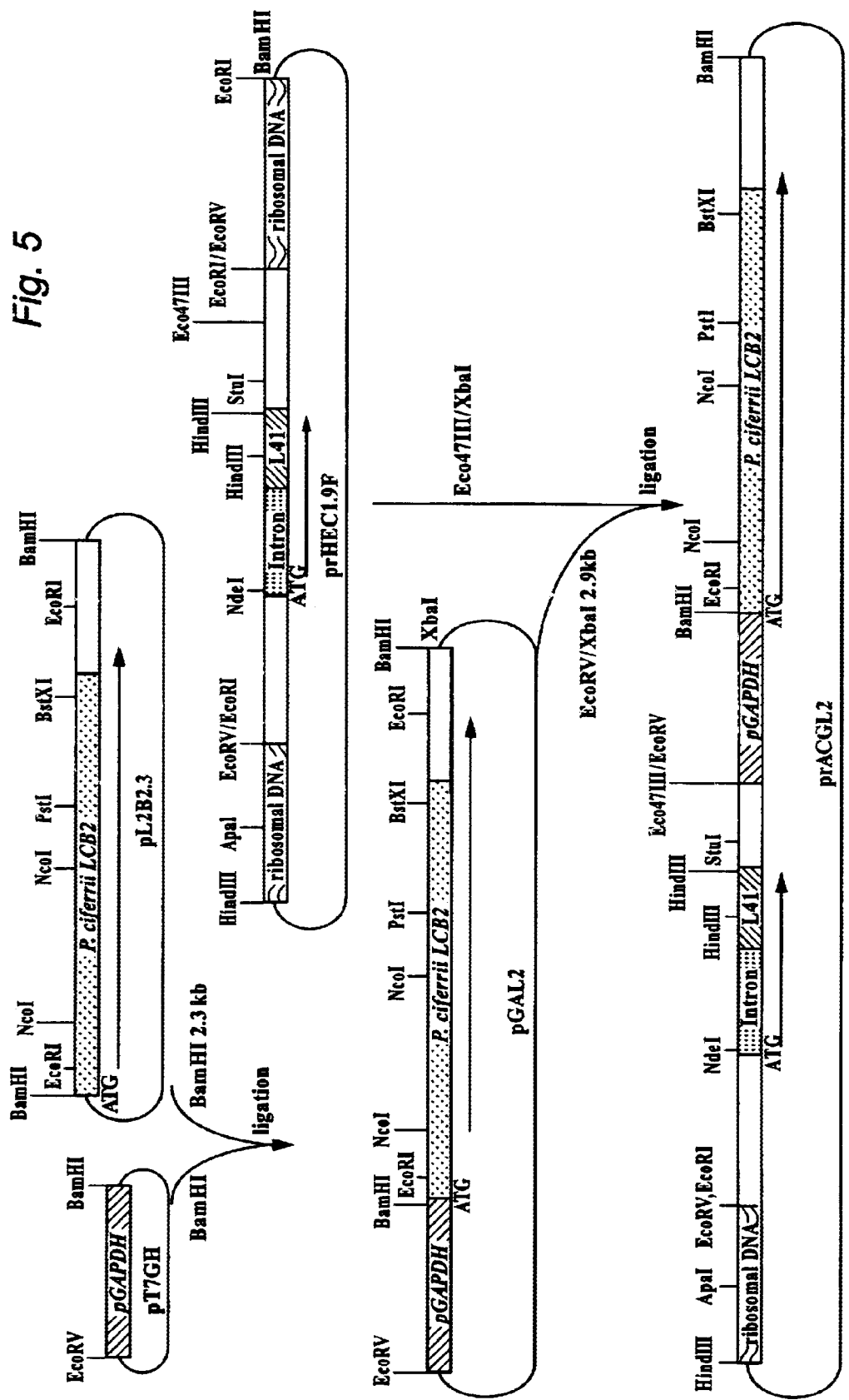

FIG. 5 represents the construction and restriction map of plasmid prACGL2.

Figure 6:
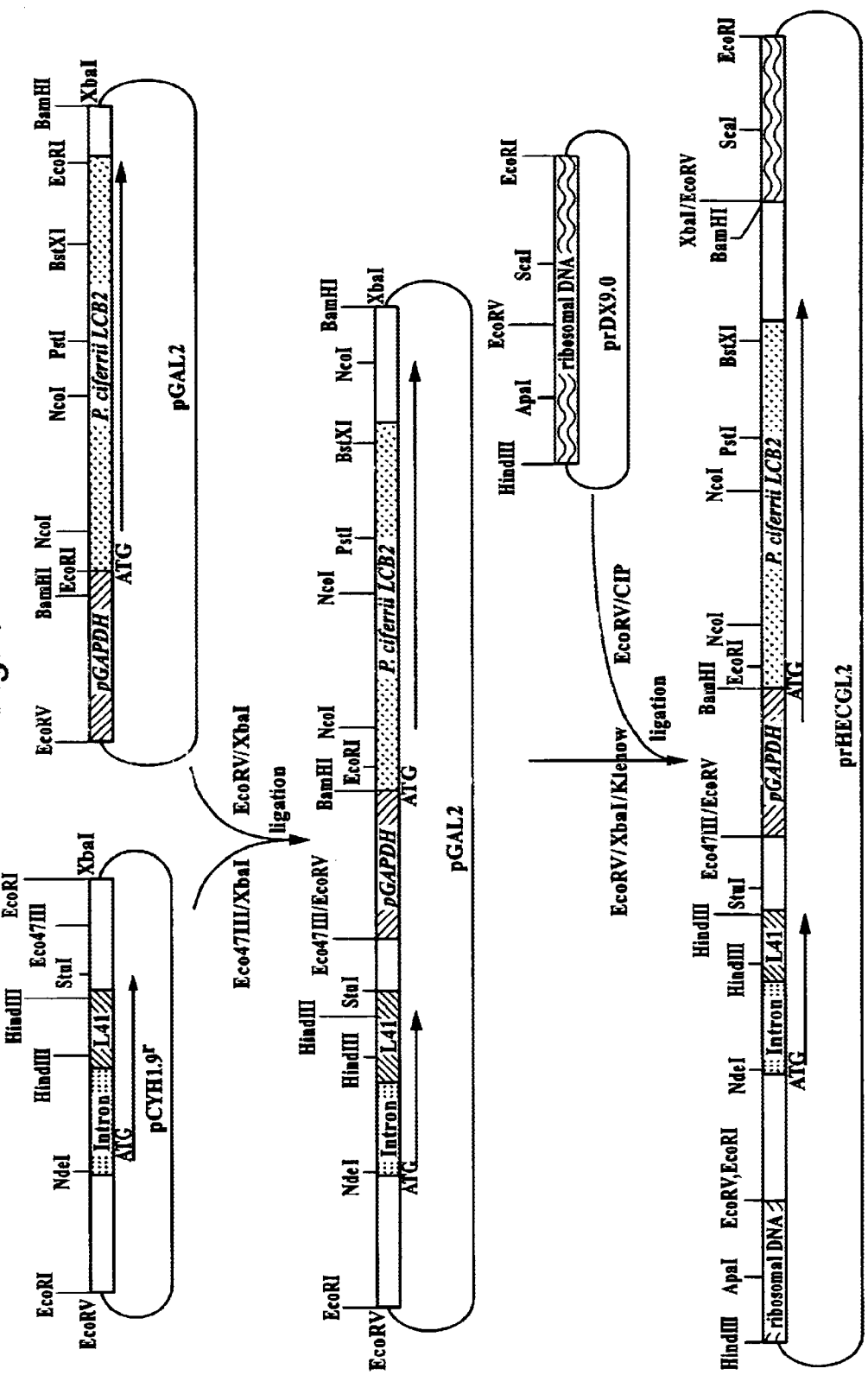
Figure 7A:
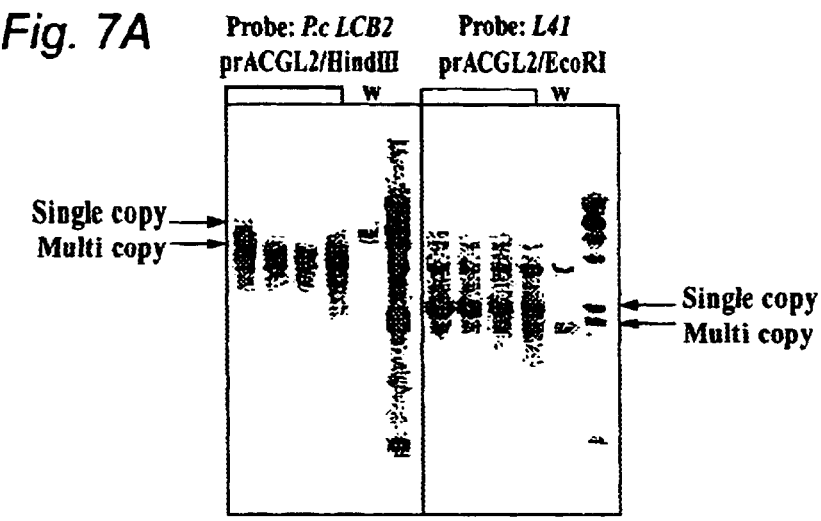
Figure 7B:
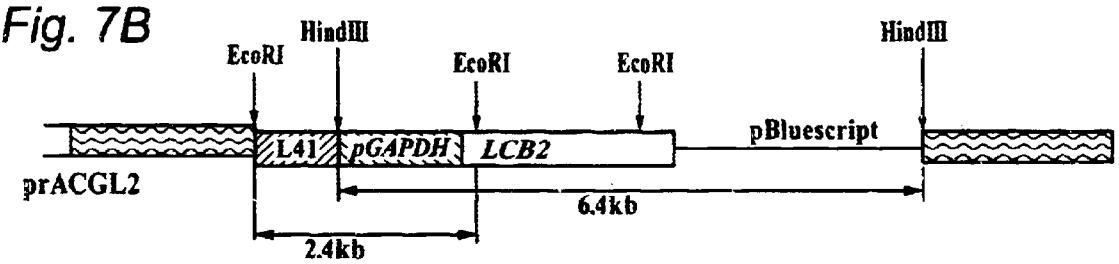
Figure 7C:
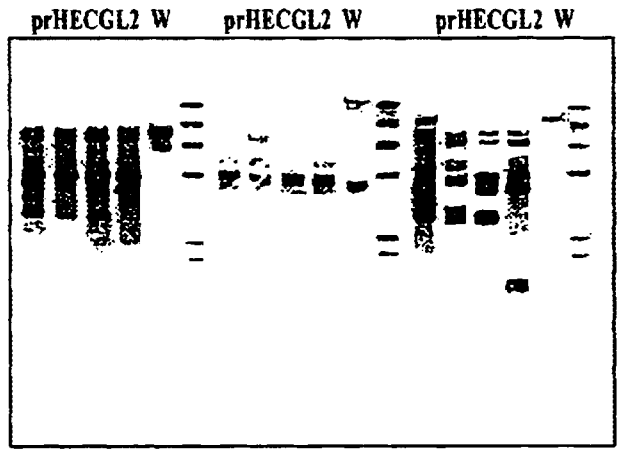
Figure 7D:
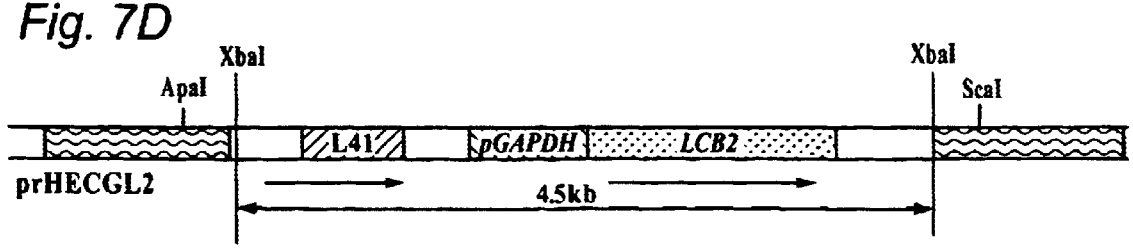

FIG. 6 represents the construction and restriction map of plasmid prHECGL2.

FIGS. 7A–7D show the results of Southern blot analysis carried out to measure the copy number of LCB2 gene transformed into host cell.

DETAILED EXPLANATION OF THE INVENTION

Kondo et al describes a transformation method for *Candida utilis* in which an antibiotic resistant gene from yeast is used as a marker gene instead of the conventional bacterial one (Kondo et al., J. Bacteriol., 177, 7171, 1995). The present inventors made attempts to apply such an idea to *Pichia ciferrii*.

For this purpose, they cloned *Pichia ciferrii* ribosomal protein L41 gene and determined its nucleotide sequence. Further, they identified 56th amino acid which is responsible for the sensitivity to cycloheximide is proline and replaced it by glutamine to give cycloheximide-resistance to L41 protein. In the present invention, L41 gene is used as a selection marker.

1. Isolation of *Pichia ciferrii* Ribosomal Protein L41 Gene

By following and modifying the method by Kondo et at (Kondo et al., J. Bacteriol., 177, 7171, 1995), two primers CYH1 and CYH4 were synthesized.

CYH1: 5'-CGC GTA GTT AAY GTN CCN AAR AC-3'

CYH4: 5'-GCC TGG CCY TTY TGY TTY TTN TC-3'

The two primers are also represented as SEQ. ID. NO; 7 and SEQ. ID. NO. 8, respectively in SEQUENCE LISTING.

PCR was performed using the two primers to isolate *Pichia ciferrii* ribosomal protein L41 gene of about 300 bp, which was labeled to be used as a probe.

Figure 1:
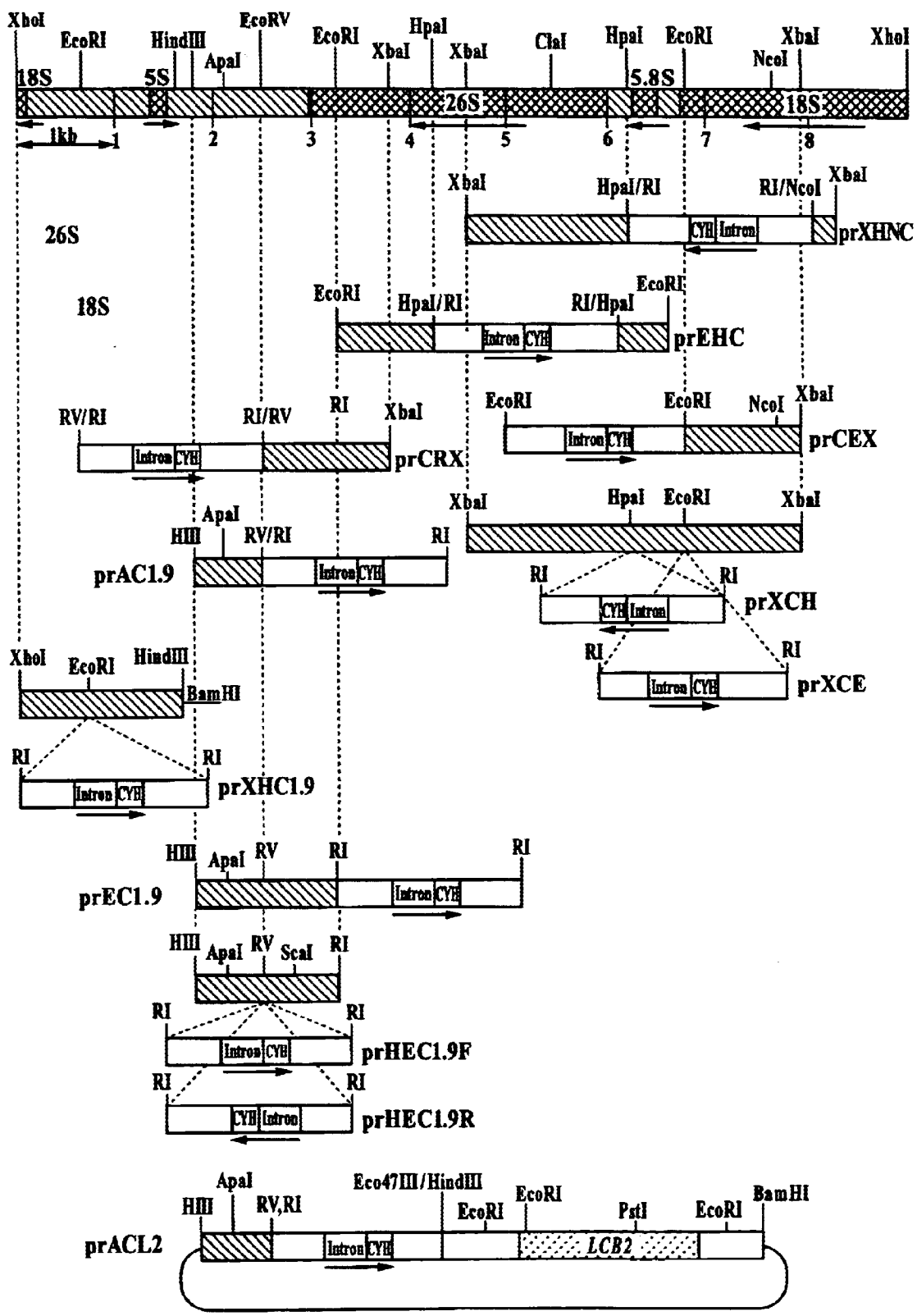
FIG. 1 is a restriction map of various plasmids having *Pichia ciferrii* ribosomal DNA incorporated with L41 genes of *Pichia ciferrii* at different sites for each plasmid, in which hatched boxes indicate ribosomal DNA fragments.

Thus obtained probe was used to carry out Southern blot analysis for *Pichia ciferrii* genome DNA. A genome DNA digested with EcoRI gives a desired band at 1.9 kb. EcoRI-digested DNA fragments of 1.9 kb was collected and used to construct pCYH1.9 which is used for nucleotide sequencing. The results are shown in FIG. 1. DNA sequence of *Pichia ciferrii* ATCC 14091 ribosomal protein L41 gene was to submitted on Mar. 7, 1998 to GenBank under accession number AF 053457. *Pichia ciferrii* ATCC 14091 ribosomal protein L41 gene has 737 base pairs including 419 bp intron. The putative amino acid sequence deduced from the nucleotide sequence shows a homology of 90% or more to those of other yeasts. It was also identified that the cycloheximide-sensitive amino acid is amino acid 56, proline.

2. Impartation of Cycloheximide Resistance to L41 Gene Construction of Plasmid PCYH1.9$^r$ for Use in the Selection of Transformed Cell.

Site-directed mutagenesis was carried out to replace proline (aa 56) in L41 gene with glutamine in order to impart cycloheximide resistance to L41 gene. Thus obtained gene-manipulated gene is designated as 'plasmid CYH1.9$^r$'.

Hereinafter, the L41 gene is indicated by an abbreviation of 'CYH' and the cycloheximide-resistant L41 gene is indicated by 'CYH$^r$' throughout the description.

3. Isolation of *Pichia ciferrii* Ribosomal DNA: Construction of Plasmid prDX9.0 for Improving Integration Efficiency of Desired Gene Into Chromosome In order to improve the efficiency of integration of the desired gene into the chromosomal DNA, ribosomal DNA was employed. Within the cell, several hundred copies of ribosomal DNA occur.

PCR primers were synthesized by using the partial nucleotide sequence of *Pichia ciferrii* ribosomal RNA (Yamada et al., Biosci. Biotechnol. Biochem., 58, 1245, 1994). PCR of *Pichia ciferrii* ATCC 14091 genome DNA was carried out by using the primers to isolate ribosomal DNA fragment of 6.0 kb. The fragment was used as a probe for Southern blot analysis to isolate *Pichia ciferrii* ATCC 14091 ribosomal DNA fragment of 9 kb, which is inserted into plasmid pBluescript KS+ to produce plasmid prDX9.0.

Partial sequence of the ribosomal DNA fragment (9 kb) was determined, and the location and orientation of 5S, 26S, 5.8S and 18S ribosomal protein genes are shown in FIG. 1.

4. Construction of Recombinant Plasmids

Ribosomal DNA was digested with various restriction enzymes and ligated to CYH$^r$ to give various plasmids as shown in FIG. 1 which will be analyzed for transformation efficiency in regard with (1) the transcription directions of respective genes; (2) the arrangement of ribosomal DNA and CYH$^r$ gene; and (3) the kind of insertion site, ribosomal RNA structural gene or non-transcribed region.

The characteristics of the plasmid in FIG. 1 are summarized in Table 1.

TABLE 1

| Plasmid | Characteristics |
|---|---|
| prXHNC | Ribosomal DNA (3.5 kb) obtained by XbaI digestion is treated with HpaI/NcoI to remove 1.6 kb ribosomal DNA and then ligated to CYH$^r$. |
| prEHC | Ribosomal DNA (3.8 kb) obtained by EcoRI digestion is treated with HpaI to remove 2 kb ribosomal DNA and then ligated to CYH$^r$. |
| prCEX | CYH$^r$ is ligated to EcoRI site of 1.1 kb ribosomal DNA obtained by EcoRI/XbaI digestion |
| prCRX | CYH$^r$ is ligated to EcoRV site of 1.3 kb ribosomal DNA obtained by EcoRV/XbaI digestion |
| prXCH | CYH$^r$ is ligated to HpaI site of 3.5 kb ribosomal DNA obtained by XbaI digestion |
| prXCE | CYH$^r$ is ligated to EcoRI site of 3.5 kb ribosomal DNA obtained by XbaI digestion |
| prXHC1.9 | CYH$^r$ is ligated to EcoRI site of 1.6 kb ribosomal DNA obtained by XbaI/HindIII digestion |
| prAC1.9 | CYH$^r$ is ligated to EcoRV site of 0.6 kb ribosomal DNA obtained by HindIII/EcoRV digestion |
| prEC1.9 | CYH$^r$ is ligated to EcoRI site of 1.4 kb ribosomal DNA obtained by HindIII/EcoRI digestion |
| prHEC1.9F | CYH$^r$ is ligated to EcoRV site of 1.4 kb ribosomal DNA obtained by HindIII/EcoRI digestion |
| prHEC1.9R | Same as prHEC 1.9F except that the insertion orientation of CYH$^r$ is reversed |

In the nomenclature of the plasmid, for example prAC, the letter 'p' indicates a plasmid, 'r' indicates that the plasmid has a ribosomal DNA, and 'C' means for 'CYH$^r$.' The letters 'A' in prAC1.9 and 'E' in prEC1.9 indicate restriction enzymes used for liberalization by digesting the ribosomal DNA. In case of other plasmids, 'X' means XbaI, 'E' means EcoRI, 'R' means EcoRV, and 'H' means HindIII, respectively. Therefore, the plasmid containing these letters in their name comprise ribosomal DNA fragments digested with these respective restriction enzymes. Moreover, numerical number after C indicates the size (base pairs) of the L41 gene, while the letter 'F' or 'R' means the orientation of ribosomal DNA fragment and CYH$^r$.

5. Transformation and Selection of Transformed Cells

The method described by Klass and Peter (Klass & Peter, Curr. Genet., 25, 305, 1994) is followed. That is to say, cells of *Pichia ciferrii* ATCC 14091 grown in YEPD medium to $OD_{600\ nm}$ of 1.5 were collected by centrifugation and mixed with the plasmid. Electroporation was performed at 500V, 50 μF and 800Ω so as to transform the cells with the plasmid and subjected to growth in YEPD solid medium to which cycloheximide was added to select transformed cells containing cycloheximide-resistant L41 gene(CYH$^r$).

The transformation efficiency is shown in Table 2 (Example 17). The data in Table 2 reveals that prHEC1.9F in which the non-transcribed region between 5S and 26S ribosomal RNA structural genes is used as an insertion site has the highest transformation efficiency. And, prHEC1.pR in which the transcription direction of 5S RNA gene is opposite to that of CYH$^r$ shows significantly decreased transformation efficiency.

6. Analysis of Transformed Cells by Southern Blot Analysis

Genomic DNA was isolated from the transformed cells and the insertion patterns of CYH$^r$ were analyzed by Southern blot analysis. As a result thereof, it was found that 4–5 copies of CYH$^r$ were present in the chromosome of the transformed cells. This result indicates that the transformation of *Pichia ciferrii* with the expression cassette of the present invention optimizes the integration of the desired gene into the chromosome of transformed *Pichia ciferrii* cells.

7. Construction of prACL2 for TAPS Production; Transformation: and the Production of TAPS by Cultivation of Transformed Cells An expression plasmid was constructed from an expression cassette comprising LCB2 gene for producing serine palmitoyl transferase and transformed into the mutant *Pichia ciferrii* KFCC-10937 to evaluate the TAPS production. The desired gene, LCB2 gene codes for serine palmitoyl transferase, which is involved in TAPS synthesis, and the mutant KFCC-10937 was developed by the inventors (KR 98-493 05A).

Serine palmitoyl transferase (3-ketosphinganine synthase, EC 2.3.1.50) is involved in the first step, which is the rate limiting step of the overall reaction, of the sphingolipids synthesis and forms 3-ketosphinganine having 18 carbon atoms by condensing serine and palmitoyl-CoA (Barenholz et al., *Biochem. Biophys. Acta*, 248, 458, 1971; ibid, 306, 341, 1973). 3-ketosphinganine serves as one of long-chain compounds in animals and as a precursor for phytosphingosine in plants and fungi.

In the present invention, the TAPS production can be significantly improved by integrating multiful copies of LCB2 gene into the chromosome of *Pichia ciferrii*. The transformed *Pichia ciferrii* cell carrying multiful copies of LCB2 gene on its chromosome produces a large amount of TAPS in a shortened time.

7-1. Isolation of LCB2 Gene Coding for Serine Palmitoyl Transferase

For the purpose of cloning the gene coding for serine palmitoyl transferase from *Pichia ciferrii* ATCC 14091 genomic DNA, probes were prepared with reference to the subunits of the known serine palmitoyl transferase gene. Serine palmitoyl transferase coding gene from *Saccharomyces cerevisiae* consists of two subunits, LCB1 and LCB2. LCB is abbreviation for 'long chain base.' (Nagiec et al., *Proc. Natl. Aca. Sci. USA*, 91, 7899, 1994). DNA sequence of LCB2 genes from other organisms such as human, mouse, *Klebsiella lactis*, and *Schizosaccharomyces pombe* (Nagiec et al., Gene, 177, 237, 1996; Hanada et al., *J. Biol. Chem.*, 272, 32108, 1997; Weiss & Stoffel, Eur. J. Biochem., 249, 239, 1997) are reported.

First, by referring the nucleotide sequence of LCB1 gene from *Saccharomyces cerevisiae* (Nagiec et al., *Proc. Natl. Aca. Sci. USA*, 91, 7899, 1994), PstI fragment (1 kb) of LCB1 gene was used as probe for Southern blot analysis of genomic DNA of *Pichia ciferrii* ATCC 14091. In this analysis, no desired band was detected. On the other hand, the Southern blot analysis using SalI fragment (0.9 kb) of LCB2 gene as probe gave DNA band of 12 kb LCB2 gene. This band was collected and inserted into plasmid pBluescript KS+ to give a library. By repeating the Southern blot analysis, ScaI/AflIII fragments (3.0 kb) were obtained and plasmid pL2SA was constructed (FIG. 2). Nucleotide sequence of LCB2 gene was determined and is represented as SEQ. ID. NO. 3 together with its putative amino acid sequence (SEQ. ID. NO. 4) in SEQUENCE LISTING. The sequence was submitted on Mar. 7, 1998 to GenBank under accession number AF053456.

*Pichia ciferrii* ATCC 14091 LCB2 gene comprises 1688 base pairs and has no intron. The putative amino acid sequence shows a high homology to that from *Saccharomyces cerevisiae*. Transmembrane helix region is present spanning the 55th–79th amino acids. The region containing lysine, which forms Schiff base together with pyridoxal phosphate, has identical amino acids sequence to those of *Saccharomyces cerevisiae*.

7-2. Construction of Plasmid prACL2

Plasmid pL2SA was treated with HindIII, Klenow and BamHI, in this order, to give a 3.0 kb fragment of LCB2 gene. This fragment was inserted to plasmid prHEC1.9F, which is treated with Eco47III and BamHI, to give plasmid prACL2.

Plasmid prACL2 has the *Pichia ciferrii* ribosomal DNA fragment, CYH$^r$(L41) and LCB2 gene, linked to each other, in this order. Plasmid prACL2 was deposited with Korea Collection of Type Cultures in Taejon on May 4, 1998 according to the Budapest Treaty on the International Recognition of the Deposit of Microorganisms for the Purposes of Patent Procedure and given an accession number of KCTC-0468BP.

7-3. Transformation

Plasmid prACL2 was transformed into the mutant *Pichia ciferrii* KFCC-10937 by following the procedure in the step 5 described above and transformed cells having a high copy number of gene were selected.

7-4. TAPS Production by Transformed Cell Cultivation

The transformed cells obtained in the step 7-3 above were cultivated in YGM optimum medium (glycerol 100 g/liter, yeast extract 2 g/liter, $KNO_3$ 3 g/liter, $(NH_4)_2SO_4$ 0.5 g/liter, $MgSO_4.7H_2O$ 0.3 g/liter, NaCl 0.5 g/liter, CSL 3 g/liter and LS-300 1 g/liter) for 4(four) days to produce TAPS.

The transformed cells according to the present invention exhibited TAPS production at least 1.3 times greater than the parent strain KFCC-10937.

8. Isolation of Glyceraldehyde-3-phosphate Dehydrogenase (GAPDH) Promoter Gene From *Pichia ciferrii*

Glyceraldehyde-3-phosphate dehydrogenase (GAPDH) is an essential enzyme involved in glycolysis and converts glyceraldehyde-3-phosphate into 1,3-bis-phosphoglycerate.

It is a constitutively expressed enzyme. Since GAPDH promoter is hardly affected by carbon source, it attracts the researchers in gene manipulation filed (Kniskem et al., Gene, 46, 135, 1986; Travis et al., J. Biol. Chem., 260, 4384, 1985; Hallewell et al., Biotechnol., 5, 363, 1987; Rosenberg et al., Method Enzymol., 185, 341, 1990; Waterham et al., Gene, 16, 37, 1997).

Based on these studies, the present inventors cloned Pichia ciferrii GAPDH promoter gene and evaluated whether the insertion of GAPDH promoter increases the expression of the desired genes.

8-1. Isolation of GAPDH Gene

GAPDH gene from Saccharomyces cerevisiae 2805 was used to clone GAPDH gene from the genomic DNA of Pichia ciferrii ATCC 14091. By using thus cloned GAPDH gene, plasmid pGH2.2 was constructed (FIG. 4). The nucleotide sequence of GAPDH gene of Pichia ciferrii ATCC 14091 was determined and is represented as SEQ. ID. NO. 5 together with its putative amino acid sequence (SEQ. ID. NO. 6) in SEQUENCE LISTING. This sequence was submitted on Mar. 7, 1998 to GenBank under accession number of AF053300.

Pichia ciferrii ATCC 14091 GAPDH gene comprises 1004 base pairs and has no intron. The nucleotide sequence and the putative amino acid sequence show 69.3% and 76.2% homology to that from Saccharomyces cerevisiae, respectively. This suggests that Pichia ciferrii ATCC 14091 GAPDH gene is new.

8-2. Isolation of GAPDH Promoter Gene

PCR using plasmid pGH2.2 and primers (primer Nos. 3 and 4; SEQ. ID. NO. 9 and SEQ. ID. NO. 10, respectively in SEQUENCE LISTING) was performed to isolate Pichia ciferrii GAPDH promoter gene (600 bp). This gene was inserted into EcoRV site of pT7-Blue T-vector to give plasmid pT7GH.

8-3. Isolation of LCB2 Gene Free of its Own Promoter

LCB2 gene free of its own promoter was isolated from plasmid pL2SA by following the procedure in FIG. 5. The gene has a size of 2.3 kb. It was inserted into BamHI site of pT7GH to give plasmid pGAL2.

8-4. Construction of Plasmid prACGL2

LCB2 gene of 2.9 kb was isolated from plasmid pGAL2 by following the procedure in FIG. 5 and inserted into Eco47III/XbaI site of prHEC1.9F to give plasmid prACGL2.

Plasmid prACGL2 has the Pichia ciferrii ribosomal DNA fragment, CYH$^r$(L41), GAPDH promoter gene and LCB2 gene, linked to each other, in this order. Its restriction map is depicted in FIG. 5. Plasmid prACGL2 was deposited with Korea Collection of Type Cultures in Taejon on Jun. 25, 1998 according to the Budapest Treaty on the International Recognition of the Deposit of Microorganisms for the Purposes of Patent Procedure and given an accession number of KCTC-0498BP.

8-5. Construction of Plasmid prHECGL2

When the host cell (e.g., strain of Pichia ciferrii) is transformed with plasmid prACGL2, the resulting transformed cell will carry genes from Pichia ciferrii as well as other undesired regions of the starting bacterial plasmid since the plasmid is treated with only one restriction enzyme for linearization prior to the transformation into the host cell. To avoid this, the present inventors add Pichia ciferrii ribosomal DNA fragment (800 bp) at the downstream of LCB2 gene of plasmid prACGL2. Thus obtained plasmid was designated as prHECGL2. (FIG. 6)

Plasmid prHECGL2 has the Pichia ciferrii ribosomal DNA fragment, CYH$^r$(L41), GAPDH promoter gene, LCB2 and Pichia ciferrii ribosomal DNA fragment, operably linked to each other, in this order. Its restriction map is depicted in FIG. 6. Plasmid prHECGL2 was deposited with Korea Collection of Type Cultures in Taejon on Aug. 10, 1998 according to the Budapest Treaty on the International Recognition of the Deposit of Microorganisms for the Purposes of Patent Procedure and given an accession number of KCTC-0511BP.

When the host cell is transformed with plasmid prHECGL2, the resulting transformed cell carry only genes from Pichia ciferrii by treating the plasmid by proper restriction enzymes to cut both of the Pichia ciferrii ribosomal DNAs. That is to say, when the plasmid prHECGL2 is transformed into Pichia ciferrii, the obtained transformed cell Pichia ciferrii will carry only endogenous genes.

8-6. Transformation

Cells of Pichia ciferrii KFCC-10937 and plasmid prACL2, prACGL2 and prBECGL2 were mixed, respectively and electroporation was performed at voltage 500V, capacity 50 $\mu$F and resistance 800$\Omega$ so as to transform the cells with the plasmid.

8-7. TAPS Production by Transformed Cell Cultivation

The transformed cells obtained in the step 8-6 above were cultivated in YGM optimum medium (glycerol 100 g/liter, yeast extract 2 g/liter, $KNO_3$ 3 g/liter, $(NH_4)_2SO_4$ 0.5 g/liter, $MgSO_4.7H_2O$ 0.3 g/liter, NaCl 0.5 g/liter, CSL 3 g/liter and LS-300 1 g/liter) to produce TAPS.

The transformed cells with plasmid prACGL2 (KCTC-0498BP) or with plasmid prHECGL2 (KCTC-0511BP) according to the present invention exhibited TAPS production at least 2.1 times and at least 1.5 times greater than the parent strain KFCC-10937 and than the transformed cell with plasmid prACL2 (KCTC-0468BP), respectively.

Free Texts in Sequence Listing

SEQ.ID.NO. 7 is an artificial sequence for PCR primer CYH1.

SEQ.ID.NO. 8 is an artificial sequence for PCR primer CYH4.

SEQ.ID.NO. 9 is an artificial sequence for PCR primer No. 3 which is used for isolation of GAPDH promoter gene.

SEQ.ID.NO. 10 is an artificial sequence for PCR primer No. 4 which is used for isolation of GAPDH promoter gene.

SEQ.ID.NO. 11 is an artificial sequence for PCR primer CH-f

SEQ.ID.NO. 12 is an artificial sequence for PCR primer CH-r.

SEQ.ID.NO. 13 is an artificial sequence for PCR primer 18R.

SEQ.ID.NO. 14 is an artificial sequence for PCR primer 26F.

SEQ.ID.NO. 15 is an artificial sequence for PCR primer L2f.

SEQ.ID.NO. 16 is an artificial sequence for PCR primer L2r.

SEQ.ID.NO. 17 is an artificial sequence for PCR primer No. 1 which is used for isolation of GAPDH gene.

SEQ.ID.NO. 18 is an artificial sequence for PCR primer No. 2 which is used for isolation of GAPDH gene.

EXAMPLES

The present invention will be described in more detail by way of various Examples, which should not be construed to limit the scope of the present invention.

Example 1

Isolation of Genomic DNA from *Pichia ciferrii* ATCC 14091

Cells of *Pichia ciferrii* ATCC 14091 grown in YEPD medium (peptone 2%, yeast extract 1% and glucose 2%) by following the method described by Johnston (Johnston et al., Yeast Genetics, molecular aspects, pp. 107–123, IRL Press, 1988) were collected and suspended in SSEM solution (1M sorbitol, 100 mM sodium citrate, 60 mM EDTA, 100 mM 2-mercaptoethanol). Novozyme was added to the suspension to a concentration of 0.1 mg/ml, and allowed to react at 37° C. for 30 minutes to give protoplast. An equal volume of SDS-TE solution (2% SDS, 50 nM EDTA in 1M Tris-Cl, pH 8.0) was added and allowed to react at 60° C. for 10 minutes to disintegrate cells. To the supernatant obtained by centrifuging at 8,000 rpm for 15 minutes, a twice volume of ethanol was added. The resulting pellets were dissolved in TE solution containing RNase to extract *Pichia ciferrii* genomic DNA.

Example 2

Isolation of L41 Gene From *Pichia ciferrii* ATCC 14091

Two following primers CYH1 and CYH4 were synthesized.

CYH1: 5'-CGC GTA GTT AAY GTN CCN AAR AC-3'

CYH4: 5'-GCC TGG CCY TTY TGY TTY TTN TC-3'

These two primers are also represented as SEQ. ID. NO. 7 and SEQ. ID. NO. 8, respectively in SEQUENCE LISTING.

PCR was performed using the two primers and *Pichia ciferrii* genomic DNA obtained in Example 1 to give L41 gene fragment of about 300 bp.

This fragment was labeled with DIG-labeling and detection kit (Boehringer Mannheim) by following the manufacturer's manual to give a probe.

Example 3

Sequencing of L41 Gene

Genomic DNA of *Pichia ciferrii* obtained in Example 1 was digested with various restriction enzymes, and the digestion products were subjected to 0.9% agarose gel electrophoresis and transferred to Nytran$^R$ membrane (Schleicher & Schuell) followed by hybridization with a hybridization solution (5×SSC, 0.1% N-laurylsarcosine, 0.02% SDS, 2% blocking agent and 30% formaldehyde) using probes obtained in Example 2. The hybridization was carried out at 42° C. for 6 hours according to the manufacturer's manual prepared by Boehringer Mannheims.

Antibodies coupled to alkaline phosphatase were introduced and BCIP and X-phosphate were added. Violet-stained band was observed.

Band is detected at 1.9 kb size of genomic DNA treated with EcoRI. This DNA fragment (1.9 kb) was collected and linked to EcoRI site of plasmid pBluescript KS+ (Stratagene) and transformed into *E. coli* DH5α to establish a library.

This library was repeatedly subjected to Southern blot analysis to isolate 1.9 kb gene fragment containing L41 gene(plasmid pCYH1.9). Nucleotide sequencing was performed for this plasmid using Automatic sequencer Model 373A (Applied Biosystem). The result is represented as SEQ. ID. NO. 1 together with its putative amino acid sequence (SEQ. ID. NO. 2) in SEQUENCE LISTING. This sequence was submitted on Mar. 7, 1998 to GenBank under accession number of AF053457.

L41 gene of *Pichia ciferrii* ATCC 14091 consists of 737 base pairs including 419 bp intron. The amino acid residue 56 is proline.

Example 4

Construction of Plasmid PCYH1.9$^r$ in Which Proline (aa 56) is Replaced by Glutamine Two primers CH-f and CH-r were prepared:

Primer CH-f: GGT CAA ACC AAA CCA GTT TTC

Primer CH-r: ATG GAA AAC TTG TTT GGT TTG ACC

These two primers are also represented as SEQ ID. NO. 11 and SEQ. ID. NO. 12, respectively in SEQUENCE LISTING.

Combinations of universal primer and primer CH-r, and of reverse primer and primer CH-f were employed for PCR using Pfu DNA polymerase and pCYH1.9 as a template to obtain two PCR products of 1.2 kb and 0.7 kb.

PCR was performed again using the two PCR products (1.2 kb and 0.7 kb), and universal and reverse primers to obtain plasmid PCYH1.9$^r$ in which proline (aa 56) is replaced by glutamine.

Example 5

Construction of Plasmid prDX9.0 Containing Ribosomal DNA Fragment

Two following primers 18R and 26F were synthesized.

Primer 18R: 5'-CAA TAA TTG CAA TGC TCT ATC CCC AGC ACG-3'

Primer 26F: 5'-GGA TAT GGA TTC TTC ACG GTA ACG TAA CTG-3'

These two primers are also represented as SEQ. ID. NO. 13 and SEQ. ID. NO. 14, respectively in SEQUENCE LISTING.

PCR was performed using the two primers and *Pichia ciferrii* genomic DNA obtained in Example 1 to give a PCR product of 6.0 kb. This PCR product was labeled in the same manner as in Example 2 to give a probe.

When the probe is subjected to Southern blot analysis with *Pichia ciferrii* genormic DNA, band is detected at 9 kb size of genomuic DNA treated with XhoI. This DNA fragment (9 kb) was collected and inserted into plasmid pBluescript KS+ (Stratagene) and its library was established. This library was repeatedly subjected to Southern blot analysis to isolate 9 kb gene fragment containing ribosomal DNA (plasmid prDX9.0).

Nucleotide sequencing was performed for this plasmid using Automatic sequencer Model 373A (Applied Biosystem). The results including the location and orientation of 26S, 18S, 5.8S and 5S ribosomal gene are shown in FIG. 1.

Example 6

Construction of Plasmid prXHNC

Plasmid prDX9.0 obtained in Example 5 was treated with XbaI to obtain 3.5 kb ribosomal DNA, which is then inserted into plasmid pBluescript KS+. The resulting recombinant plasmid is treated with HpaI/NcoI/Klenow to remove 1.6 kb ribosomal DNA and linked to 1.9 kb CYH$^r$ gene, which was obtained by digesting plasmid pCYH1.9$^r$ in Example 4 with EcoRI/Klenow, to obtain plasmid prXHC.

Example 7

Construction of Plasmid prEHC

Plasmid prDX9.0 obtained in Example 5 was treated with EcoRI to obtain 3.8 kb ribosomal DNA, which is then inserted into plasmid pbluescript KS+. The resulting recombinant plasmid is treated with HpaI to remove 2 kb ribosomal DNA and Linked to 1.9 kb CYH$^r$ gene, which was obtained by digesting plasmid pCYH1.9$^r$ in Example 4 with EcoRI/Klenow, to obtain plasmid prEHC.

Example 8

Construction of Plasmid prCEX

Plasmid prDX9.0 obtained in Example 5 was treated with EcoRI/XbaI to obtain 1. 1 kb ribosomal DNA. 1.9 kb CYH$^r$ gene, which was obtained by digesting plasmid pCYH1.9$^r$ in Example 4with EcoRI/Klenow, was linked to EcoRI site of the 1.1 kb ribosomal DNA to give plasmid prCEX.

Example 9

Construction of Plasmid prCRX

Plasmid prDX9.0 obtained in Example 5 was treated with EcoRV/XbaI to obtain 1.3 kb ribosomal DNA. 1.9 kb CYH$^r$ gene, which was obtained by digesting plasmid pCYH1.9$^r$ in Example 4 with EcoRI/Klenow, was lined to EcoRV site of the 1.3 kb ribosomal DNA to give plasmid prCRX.

Example 10

Construction of Plasmid prXCH

Plasmid prDX9.0 obtained in Example 5 was treated with XbaI to obtain 3.5 kb ribosomal DNA. 1.9 kb CYH$^r$ gene, which was obtained by digesting plasmid PCYH1.9$^r$ in Example 4 with EcoRI/Klenow, was linked to HpaI site of the 3.5 kb ribosomal DNA to give plasmid prXCH.

Example 11

Construction of Plasmid prXCE

Plasmid prDX9.0 obtained in Example 5 was treated with XbaI to obtain 3.5 kb ribosomal DNA. 1.9 kb CYH$^r$ gene, which was obtained by digesting plasmid pCYH1.9$^r$ in Example 4 with EcoRI, was linked to EcoRI site of the 3.5 kb ribosomal DNA to give plasmid prXCE.

Example 12

Construction of Plasmid prXHC1.9

Plasmid prDX9.0 obtained in Example 5 was treated with XhoI/HindIII to obtain 1.6 kb ribosomal DNA. A plasmid containing this 1.6 kb ribosomal DNA was digested with HindIII/Klenow to give ribosomal DNA. 1.9 kb CYH$^r$ gene, which was obtained by digesting plasmid pCYH1.9$^r$ in Example 4 with EcoRI, was linked to EcoRI site of the HindIII/Klenow digestion product to give plasmid prXHC1.9.

Example 13

Construction of Plasmid prAC1.9

Plasmid prDX9.0 obtained in Example 5 was treated with HindIII/EcoRV to obtain 0.6 kb ribosomal DNA. 1.9 kb CYH$^r$ gene, which was obtained by digesting plasmid pCYH1.9$^r$ in Example 4 with EcoRI/Klenow, was linked to EcoRV site of the 0.6 kb ribosomal DNA to give plasmid prAC1.9.

Example 14

Construction of Plasmid prEC1.9

Plasmid prDX9.0 obtained in Example 5 was treated with HindIII/EcoRI to obtain 1.4 kb ribosomal DNA. 1.9 kb CYH$^r$ gene, which was obtained by digesting plasmid pCYH1.9$^r$ in Example 4 with EcoRI, was linked to EcoRI site of the 1.4 kb ribosomal DNA to give plasmid prXCH.

Example 15

Construction of Plasmid prHEC1.9F

Plasmid prDX9.0 obtained in Example 5 was treated with HindIII/EcoRI to obtain 1.4 kb ribosomal DNA. 1.9 kb CYH$^r$ gene, which was obtained by digesting plasmid pCYH1.9$^r$ in Example 4 with EcoRI/Klenow, was linked to EcoRV site of the 1.4 kb ribosomal DNA to give plasmid prHEC1.9F.

Example 16

Construction of Plasmid prHEC1.9R

The procedure in Example 15 was repeated except that the insertion orientation of CYH$^r$ was opposite to that of Example 5 to obtain plasmid prHEC1.9R.

Example 17

Transformation Efficiency of Plasmids

The method described by Klass and Peter (Klass & Peter, Curr. Genet., 25, 305, 1994) was followed. That is to say, cells of *Pichia ciferrii* KFCC-10937 grown in YEPD medium (100 ml) to OD$_{600\ nm}$ of 1.5 were collected by centrifugation and dispersed in 50 mM phosphate buffer (pH 7.5; 40 ml), to which 25 mM DTT was added, at 37° C. for 15 minutes. The mixture was washed twice with ice-cooled stabilization solution (100 ml; 270 mM sucrose, 10 mM Tris-Cl (pH 7.5), 1 mM MgCl$_2$) and suspended in 1 ml of stabilization solution.

To the resulting suspension (50 microliters), 5 microliters of the solution of respective plasmids obtained in Examples 6–16 are added and allowed to stand on ice for 10 minutes. Then, the solution was transferred to 0.2 mm electroporation cuvettes (Bio-Rad). Electroporation was carried out using Gene-pulser II (Bio-Rad) at 500V, 50 μF and 800Ω, and the electroporation product was suspended into 0.5 mL of stabilization solution. After adding 2 mL of YEPD medium, the cultivation was carried out at 25° C. for 5 hours. Then the culture broth was plated on YEPD solid medium, to which 10 μg/mL of cycloheximide was added, at 25° C. for 4–5 days. The number of transformed cells was counted and transformation efficiency was shown in Table 2.

TABLE 2

| Plasmid | No. of transformed cell per μg | Plasmid | No. of transformed cell per μg |
|---|---|---|---|
| prXHNC | 276 | prEHC | 250 |
| prCEX | 194 | prCRX | 226 |

TABLE 2-continued

| Plasmid | No. of transformed cell per µg | Plasmid | No. of transformed cell per µg |
|---|---|---|---|
| prXCH | 314 | prXCE | 134 |
| prAC1.9 | 1574 | prXHC1.9 | 1287 |
| prEC1.9 | 983 | prHC1.9F | 1760 |
| prHEC1.9R | 54 | | |

The results in Table 2 reveals that the site of ribosomal DNA where CYH$^r$ gene is inserted and the transcription direction of CYH$^r$ gene are closely related with the transformation efficiency. Plasmids prAC1.9 and prHEC1.9F in which the non-transcribed region between 5S and 26S ribosomal RNA structural genes is used as an insertion site has the highest transformation efficiency. And, prHEC1.9R in which the transcription direction of 5S RNA gene is opposite to that of CYH$^r$ shows significantly decreased transformation efficiency.

Based on these results, plasmid prHEC1.9F was selected.

Example 18

Selection of Transformation Conditions

In order to establish the optimum conditions of transformation, linear prHEC1.9 obtained after treating with ApaI/ScaI was transformed by following the procedure in Example 17 except that the voltage was changed to 500, 600 or 700V and the resistance to 100, 200, 300, 400, 500, 600, 700 or 800Ω while keeping the capcity of 50 µF. The results are shown in Table 3.

TABLE 3

| Voltage (V) | Resistance (Ω) | No. of transformed cell per µg |
|---|---|---|
| 500 | 100 | 0 |
| | 200 | 82 |
| | 300 | 1065 |
| | 400 | 1770 |
| | 500 | 2890 |
| | 600 | 4250 |
| | 700 | 6300 |
| | 800 | 6850 |
| 600 | 100 | 0 |
| | 200 | 210 |
| | 300 | 1488 |
| | 400 | 2644 |
| | 500 | 5250 |
| | 600 | 6750 |
| | 700 | 6500 |
| | 800 | 4740 |
| 700 | 100 | 18 |
| | 200 | 620 |
| | 300 | 2360 |
| | 400 | 4400 |
| | 500 | 3840 |
| | 600 | 2640 |

The results in Table 3 confirm that the optimum transformation conditions are capacity 50 µF, voltage 500V and resistance 800Ω.

Example 19

Analysis of Transformed Cell by Southern Blot Analysis

Each of transformed cells selected in Example 17 was inoculated into YEPD medium to which 5 µg/mL of cycloheximide was added and subjected to cultivation while agitation at 25° C. for 18–20 hours, followed by centrifugation to collect cell pellets. Thus obtained cells were placed in 1.5 mL tubes. Cells were suspended in 30 µL of STES solution (0.5M NaCl, 0.01M EDTA, 1% SDS in 0.2M Tris-Cl, pH 7.6) and 0.8 volumes of glass beads (diameter 0.4 mm) were added thereto. The mixtures were stirred for 5 minutes, 200 µL of TE buffer (1 mM EDTA in 10 mM Tris-Cl, pH 8.0) and 200 µL of phenol/chloroform/isoamylalcohol (25:24:1) were added. The resulting mixtures were stirred for 2 minutes and centrifuged at 12,000 rpm. 2.5 Volumes of ethanol was added to the supernatant to precipitate genomic DNA and dried.

Genomic DNA (2–3 µg) was dissolved into 50 ∞L of distilled water, treated with EcoRI, and subjected to electrophoresis on 0.8% agarose gel. Southern blot analysis was carried out by using L41 gene in Example 2 as a probe to detect bands. It was observed that 4–5 copies of L41 gene are carried on genomic DNA of all transformed cells.

Example 20

Construction of Plasmid prACL2

(1) Isolation of LCB2 Gene From *Pichia ciferrii* ATCC 14091.

Cells of *Saccharomyces cerevisiae* grown in YEPD medium (peptone 2%, yeast extract 1% and glucose 2%) by following the method described by Johnston (Johnston et al., Yeast Genetics, molecular aspects, pp.107–123, IRL Press, 1988) were collected and genomic DNA was isolated therefrom.

Two following primers L2f and L2r were synthesized.

Primer L2f: 5'-ATG AGT ACT CCT GCA AAC TA-3'
Primer L2r: 5'-TAA CAM AAT ACT TGT CGT CC-3'

These two primers are also represented as SEQ. ID. NO. 15 and SEQ. ID. NO. 16, respectively in SEQUENCE LISTING.

PCR was performed using the two primers and the *Saccharomyces cerevisiae* genomic DNA obtained in the above to give LCB2 gene fragment of about 1680 bp. The SalI fragment of 913bp was labeled with DIG-labeling and detection kit (Boehringer Mannheim) by following the manufacturer's manual to give a probe.

Genomic DNA of *Pichia ciferrii* obtained in Example 1 was digested with various restriction enzymes, BamHI, EcoRI, EcoRV, HindIII, PstI or SalI, and the digestion products were subjected to electrophoresis in TAE buffer and transferred to Nytran$^R$ membrane (Sckleicher & Schuell) followed by Southern blot analysis.

The Southern blot analysis was carried out using a hybridization solution (5×SSC, 0.1% N-laurylsarcosine, 0.02% SDS, 2% blocking agent and 30% formamide) at 42° C. for 6 hours according to the manufacturer's manual prepared by Boehringer Mannheims.

Antibodies coupled to alkaline phosphatase were introduced and BCIP and X-phosphate were added. Violet color-stained bands were observed.

Band is detected at 12 kb size of genomic DNA treated with HindIII.

This DNA fragment(12kb) was collected and inserted into plasmid pBluescript KS+ (Stratagene) and transformed into *E. coli* DH5α to establish a library.

This library was repeatedly subjected to Southern blot analysis to isolate 3.0 kb SacI/AflIII fragment containing LCB2 gene(plasmid pL2SA).

Restriction map and sequencing of *Pichia ciferrii* LCB2 gene are shown in FIG. 2. The nucleotide sequence is represented as SEQ. ID. NO. 3 together with its putative amino acid sequence (SEQ. ID. NO. 4) in SEQUENCE LISTING. The nucleotide sequence was submitted on Mar. 7, 1998 to GenBank under accession number of AF053456.

LCB2 gene of *Pichia ciferrii* ATCC 14091 consists of 1688 base pairs without intron, and its putative amino acid sequence shows a high homology to that of *Saccharomyces cerevisiae*.

(2) Construction of Plasmid prACL2

Plasmid prHEC1.9F obtained in Example 15 was digested with Eco47III/BamHI to give a linear one. On the other hand, plasmid pL2SA obtained in (1) above was treated with HindIII, Klenow and BamHI, in this order, to give a 3.0 kb fragment of LCB2 gene. This 3.0 kb fragment was inserted to the above linear plasmid to give plasmid prACL2. (FIG. 3)

Plasmid prACL2 has the *Pichia ciferrii* ribosomal DNA fragment, CYH'(L41) and LCB2 gene, linked to each other, in this order. Plasmid prACL2 was deposited with Korea Collection of Type Cultures in Taejon on May 4, 1998 according to the Budapest Treaty on the International Recognition of the Deposit of Microorganisms for the Purposes of Patent Procedure and given an accession number of KCTC-0468BP.

Example 21

Transformation

Plasmid prACL2 was linearized with ApaI and transformed into the mutant *Pichia ciferrii* KFCC-10937 by following the procedure in Example 17. $10^2$–$10^3$ colonies per µg of plasmid were formed. Twelve largest colonies were selected.

Each of transformed cells was inoculated into YEPD medium to which 5 µg/mL of cycloheximide was added and subjected to cultivation while agitation at 25° C. for 18–20 hours, followed by centrifugation to collect cell pellets. Thus obtained cells were placed in 1.5 mL tubes. Cells were suspended in 30 µL of STES solution (0.5M NaCl, 0.01M EDTA, 1% SDS in 0.2M Tris-Cl, pH 7.6) and 0.8 volumes of glass beads (diameter 0.4 mm) were added thereto. The mixtures were stirred for 5 minutes, 200 µL of TE buffer (1 mM EDTA in 10 mM Tris-Cl, pH 8.0) and 200 µL of phenol/chloroform/isoamylalcohol (25:24:1) were added. The resulting mixtures were stirred for 2 minutes and centrifuged at 12,000 rpm. 2.5 Volumes of ethanol was added to the supernatant to precipitate genomic DNA and dried.

Genomic DNA (2–3 µg) was dissolved into 50 µL of distilled water, treated with EcoRI, and subjected to electrophoresis on 0.8% agarose gel. Southern blot analysis was carried out by using L41 gene in Example 2 as a probe to detect bands. It was observed that 5–10 copies of L41 gene are carried on genomic DNA of all transformed cells. One of them is picked up and named as 'Transformed cell 1.'

Comparative Example 1

TAPS Production by Strain KFCC-10937 Cultivation

The parent strain KFCC-10937 was cultivated in 100 ML of YGM optimum medium (glycerol 100 g/liter, yeast extract 2 g/liter, $KNO_3$ 3 g/liter, $(NH_4)_2SO_4$ 0.5 g/liter, $MgSO_4 \cdot 7H_2O$ 0.3 g/liter, NaCl 0.5 g/liter, CSL 3 g/liter and LS-300 1 g/liter) at 25° C. and 250 rpm for 4 days. After standing at 25° C. for 2 days, 4 volumes of mixed solvent of chloroform/methanol (1:1) was added to separate phases and extract TAPS.

TAPS was analyzed on HPLC using ELSD(Electron Light Scanning Detector). As solvent, a mixture of iso-octane and THF/formic acid (100:1.5) varying its ratio 9:1, 7:3 and then 9:1 was used.

Example 22

TAPS Production by Transformed Cell 1

Transformed cell 1 obtained in Example 20 was cultivated in the same condition and manner as in Comparative Example 1 to produce TAPS.

TAPS productions in Comparative Example 1 and Example 22 are shown in Table 4.

TABLE 4

|  | KFCC-10937 | Transformed cell 1 |
| --- | --- | --- |
| Doubling Time (hr) | 1.5 | 1.5 |
| Biomass concentration (g/L) | 41.6 | 43.6 |
| Amount of TAPS (mg/L) | 5206 | 7444 |
| TAPS specific yield (mg/gdw*) | 125.1 | 170.7 |
| Volume productivity (mg TAPS/L/hr) | 54.2 | 77.5 |

*gdw = dry weight (g)

The results in Table 4 affirmed that the transformation of *Pichia ciferrii* with the expression cassette according to the present invention makes it possible to maximize the integration of the desired gene onto the chromosome of the host.

Example 23

Preparation of Probe for GAPDH Gene Cloning

Two following primers (Primer No. 1 and No. 2) were synthesized.

Primer 1: 5'-ATG GTT AGA GTT GCT ATT AAC G-3'
Primer 2: 5'-AAG CCT TGG CAA TGT GTT CAA-3'

These two primers also represented as SEQ. ID. NO. 17 and SEQ. ID. NO. 18, respectively in SEQUENCE LISTING.

PCR was performed using the two primers to isolate 1 kb GAPDH gene from *Saccharomyces cerevisiae* 2805 (provided by courtesy of R. B. Wickner at NIH). The gene was inserted into EcoRV site of plasmid pT7-Blue T-vector (Novagen) to obtain plasmid pT7-SGH.

Plasmid pT7-SGH was digested with XbaI and SalI to give 0.9 kb gene fragment, which was labeled with DIG-labeling and detection kit (Boehringer Mannheim) by following the manufacturer's manual to give a probe.

Example 24

Isolation of GAPDH Gene from *Pichia ciferrii*

Genomic DNA of *Pichia ciferrii* obtained in Example 1 was digested with various restriction enzymes, BamHI, EcoRI, EcoRV, HindIII, PstI or SalI, and the digestion products were subjected to electrophoresis on 0.9% agarose gel and transferred to Nytran$^R$ membrane (Schleicher & Schuell) followed by Southern blot analysis using the probe obtained in Example 23.

The Southern blot analysis was carried out using a hybridization solution (5×SSC, 0.1% N-laurylsarcosine, 0.02% SDS, 2% blocking agent and 30% formamide) at 42° C. for 6 hours according to the manufacturer's manual prepared by Boehringer Mannheim.

Antibodies coupled to alkaline phosphatase were introduced and BCIP and X-phosphate were added. Violet color-stained bands were observed at about 6 kb sized fragment of the genomic DNA treated with HindIII/EcoRI.

This DNA fragment (about 6 kb) was collected and inserted into plasmid pBluescript KS+ (Stratagene) and transformed into *E. coli* DH5α to establish a library. This library was repeatedly subjected to Southern blot analysis to isolate 6.0 kb AflIII/HindIII fragment containing GAPDH gene(plasmid pGH2.2).

The restriction map and sequencing of GAPDH gene of *Pichia ciferrii* ATCC 14091 are shown in FIG. 4. The nucleotide sequence is represented as SEQ. ID. NO. 5 together with its putative amino acid sequence (SEQ. ID. NO. 6) in SEQUENCE LISTING. This sequence was submitted on Mar. 7, 1998 to GenBank under accession number of AF053300.

*Pichia ciferrii* ATCC 14091 GAPDH gene comprises 1004 base pairs and has no intron. The nucleotide sequence and the putative amino acid sequence show 69.3% and 76.2% homology to that from *Saccharomyces cerevisiae*, respectively.

Example 25

Isolation of *Pichia ciferrii* GAPDH Promoter Gene

Two following primers (Primer No. 3 and No. 4) were synthesized.

Primer 3: 5'-GAT ATC TAC ATA CAA TTG ACC CAT AG-3'

Primer 4: 5'-GGA TCC TTA ATT ATT TGT TTG TTT-3'

These two primers are also represented as SEQ. ID. NO. 9 and SEQ. ID. NO. 10, respectively in SEQUENCE LISTING.

PCR using plasmid pGH2.2 obtained in Example 24 and the two primers (primer Nos. 3 and 4) was performed to isolate *Pichia ciferrii* GAPDH promoter gene (600 bp). This gene was inserted into EcoRV site of pT7-Blue T-vector to give plasmid pT7GH.

Example 26

Isolation of LCB2 Gene Free of its Own Promoter

Plasmid pL2SA obtained in Example 20 was treated with AflIII to give promoter-free LCB2 gene (2.3 kb). This 2.3 kb gene was treated with Klenow and inserted into plasmid pBluescript KS+ treated with BamHI/Klenow to give plasmid pL2B2.3. (FIG. 5)

Plasmid pL2B2.3 was digested with BamHI to give 2.3 kb LCB2 gene, which was inserted to BamHI site of plasmid pT7GH in Example 4 to give pGAL2.

Example 27

Construction of Exression Cassette

Plasmid prHEC1.9F obtained in Example 15 was linearized by treating with Eco47III and XbaI. GAPDH promoter/ LCB2 gene (2.9 kb) obtained by treating plasmid pGAL2 (Example 26) with EcoRV and XbaI was inserted to the linear plasmid prHEC1.9F to give prACGL2. (FIG. 5)

Plasmid prACGL2 has the *Pichia ciferrii* ribosomal DNA fragment, CYH$^r$(L41), GAPDH promoter gene and LCB2 gene, linked to each other, in this order. Plasmid prACGL2 was deposited with Korea Collection of Type Cultures in Taejon on Jun. 25, 1998 according to the Budapest Treaty on the International Recognition of the Deposit of Microorganisms for the Purposes of Patent Procedure and given an accession number of KCTC-0498BP.

Plasmid pCYH1.9$^r$ obtained in Example 4 was linearized by treating with Eco47III and XbaI. GAPDH promoter/ LCB2 gene (2.9 kb) obtained by treating plasmid pGAL2 (Example 26) with EcoRV and XbaI was inserted to the linear plasmid pCYH1.9$^r$ to give pCHGL2. (FIG. 6). This plasmid was treated with EcoRV/XbaI/Klenow to give 4.6 kb CYH$^r$/GAPDH promoter/LCB2 gene which is then inserted to EcoRV site of 1.4 kb ribosomal DNA, which was obtained by treating plasmid prDX9.0 (Example 5) with HindIII/EcoRI, to give plasmid prHECGL2. (FIG. 6)

Plasmid prHECGL2 has a structure that it contains additional *Pichia ciferrii* ribosomal DNA fragment (800 bp) linked at downstream of LCB2 gene of plasmid prACGL2. That is to say, plasmid prHECGL2 contains *Pichia ciferrii* ribosomal DNA fragment, CYH$^r$(L41), GAPDH promoter gene, LCB2 and *Pichia ciferrii* ribosomal DNA fragment, operatively linked to each other, in this order.

Plasmid prHECGL2 was deposited with Korea Collection of Type Cultures in Taejon on Aug. 10, 1998 according to the Budapest Treaty on the International Recognition of the Deposit of Microorganisms for the Purposes of Patent Procedure and given an accession number of KCTC-0511BP.

Plasmid prHECGL2 is distinguished from and advantageous over plasmid prACGL2 that the former introduces only *Pichia ciferrii* endogenous genes onto the chromosome of *Pichia ciferrii* transformed cell while the latter introduces *Pichia ciferrii* endogenous genes together with bacterial genes (originated from plasmid pBluescript KS+) when they are used to transform *Pichia ciferrii*.

Example 28

Transformation

Plasmid prACGL2 (Example 27) and prHECGL2 (Example 27) were linearized with ApaI and ApaI/ScaI, respectively. Then, these linear plasmids were transformed into *Pichia ciferrii* KFCC-10937 by following the procedure in Example 17. $10^3$ colonies per μg of plasmid were formed. Four largest colonies were selected for respective plasmid-transformed cells.

Each of transformed cells was inoculated into YEPD medium to which 5 μg/mL of cycloheximide was added and subjected to cultivation while agitation at 25° C. for 18–20 hours, followed by centrifugation to collect cell pellets. Thus obtained cells were placed in 1.5 mL tubes. Cells were suspended in 30 μL of STES solution (0.5M NaCl, 0.01M EDTA, 1% SDS in 0.2M Tris-Cl, pH 7.6) and 0.8 volumes of glass beads (diameter 0.4 mm) were added thereto. The mixtures were stirred for 5 minutes, 200 μL of TE buffer (1 mM EDTA in 10 mM Tris-Cl, pH 8.0) and 200 μL of phenol/chloroform/isoamylalcohol (25:24:1) were added. The resulting mixtures were stirred for 2 minutes and centrifuged at 12,000 rpm. Two and half (2.5) volumes of ethanol was added to the supernatant to precipitate genomic DNA and dried.

Genomic DNA (2–3 μg) was dissolved into 50 μL of distilled water, treated with HindIII, EcoRI or XbaI, and subjected to electrophoresis on 0.8% agarose gel. Southern blot analysis was carried out by using DIG-labeled L41 gene, DIG-labeled LCB2 gene or DIG-labeled GAPDH promoter gene as a probe to detect bands (FIGS. 7A–7D). It was observed that about 4–5 copies of the genes are carried on genomic DNA of all transformed cells. Each one of the respective prACGL2-transformed and prHECGL2-transformed cells is picked up and named as 'Transformed cell 2' and 'Transformed cell 3,' respectively.

Example 29

TAPS Production by Transformed Cell 2

Transformed cell 2 obtained in Example 28 was cultivated in the same condition and manner as in Comparative Example 1 to produce TAPS. TAPS production is shown in Table 5.

TABLE 5

|  | Transformed cell 2 (prACGL2) |
| --- | --- |
| Doubling Time (hr) | 1.5 |
| Biomass concentration (g/L) | 40.1 |
| Amount of TAPS (mg/L) | 10933 |
| TAPS specific yield (mg/gdw*) | 272.6 |
| Volume productivity (mg TAPS/L/hr) | 113.9 |

*gdw = dry weight (g).

Example 30 and Comparative Example 2

TAPS Production by Transformed Cell 3

Transformed cell 2 obtained in Example 28 or parent strain of *Pichia ciferrii* was cultivated in YMGL medium (yeast extract 3 g/L, malt extract 3 g/L, glycerol 30 g/L) under the same conditions as that in Comparative Example 1 to produce TAPS. TAPS productions are shown in Table 6.

TABLE 6

|  | Parent Strain (KFCC-10937) | Transformed cell 3 (prHECGL2) |
| --- | --- | --- |
| TAPS in mg/mL | 0.200 | 0.420 |
| TAPS in g/g cell | 0.012 | 0.027 |

The results in Table 6 reveal that the absolute production of TAPS in YMGL medium decreases when compared to that in YGM optimum medium, and that the TAPS production by transformed cell 3 is 2.1 times greater than that of the parent strain.

In summary, the present invention has following advantages:

(1) The expression cassette of the present invention allows a maximized integration of desired genes into chromosome of host *Pichia ciferrii* cells.

(2) Plasmid prACL2 according to the present invention has 0.6 kb *Pichia ciferrii* ribosomal DNA fragment, CYH$^r$ (L41) and LCB2 gene coding for serine palmitoyl transferase, operatively linked to each other, in this order. It shows a good efficiency of transformation into host cells and the resulting transformed cells show at least 1.3 times greater TAPS production than the parent strain.

(3) Introduction of GAPDH promoter gene into the expression cassette according to the present invention allows a further increase in the expression of the desired gene in the transformed cell.

(4) Plasmid prACGL2 according to the present invention has 0.6 kb *Pichia ciferrii* ribosomal DNA fragment, CYH$^r$ (L41), glyceraldehyde-3-phosphate dehydrogenase (GAPDH) promoter gene and LCB2 gene, and plasmid prHECGL2 has further *Pichia ciferrii* ribosomal DNA fragment of 800 bp at the downstream of the LCB2 gene in plasmid prACGL2. These plasmids show an excellent transformation efficiency as well as show TAPS production at least 2.1 times greater than the parent strain KFCC-10937 due to an increased expression of LCB2 gene by action of GAPDH promoter.

Although preferred embodiments of the present invention have been described in detail herein above, it should be clearly understood that many variations and/or modifications of the basic inventive concepts herein taught which may appear to those skilled in the art will still fall within the spirit and scope of the present invention as defined in the appended claims.

---

```
<160> NUMBER OF SEQ ID NOS: 18

<210> SEQ ID NO 1
<211> LENGTH: 1906
<212> TYPE: DNA
<213> ORGANISM: Pichia ciferrii
<220> FEATURE:
<221> NAME/KEY: CDS
<222> LOCATION: (603)..(605)
<221> NAME/KEY: CDS
<222> LOCATION: (1025)..(1348)
<221> NAME/KEY: intron
<222> LOCATION: (606)..(1024)

<400> SEQUENCE: 1
gaattctctt aaatgatgtt ggattaaaaa ccttgatcct ttctcttgaa tataaatata      60
tcactttcaa accagttgaa tatgtgaagt agtttggttg ttgatgtagt ttaaatctgt     120
attctatttt tggtgtagat ctgtatatgt caattacttt ttttttttcct cgtacaattt    180 caagtttaca aacaagtgga aatgtaaaca accacgcgtt tcaaaaaaaa agttctgttc     240
tagatctaag acacctagtc aggtgatatt aagctagggc tatatgattg atgtttgctc     300
aaaagatgtg actgtctgga aatgaaaatt ctagcagtgg tgttcagatg ttccttgcacc    360
```

```
aaccaacaaa ctctgaacaa ttcgcgaagc aaacaacact aacacacgtg attatgtcat    420
caattcatga tctttctct tagatttcgc gattcaagcc agagtggtgt ttgggttggg    480 cactttttt ttctgtattc gcagagactc agtgttggtt tttcaaaagt gttgaaattt    540
aatactcttt ttgtagtagt tattatagag accatcatta aaaggtacaa catcagttaa    600 aa atg ggtatgtcca tatgaagtta agatacaaga ggatcagtgt atgagtagag        655
   Met
   1 aatcacaatc atgtcaatgt tgttatttga atcgttgtca aaagtgtaat tttgtttgtt    715 caatgttgaa atttataatt tgaaagattt aagcaaagtt caaggggcaa agaataaag    775 aatacaagag taatgaaaga ttaaagaagt aatacaagct attgagagaa gattcattca    835 gatatagtta agatcacaag tgacagaagt tttaaatgat ttcagtaatt tttaatccat    895 attcataacc tacaaagtta agatgatcaa acaatattga gaataaagat acaaatgtat    955 tcaaaccact caactatcct acttgaatcc aaaatctatg atttgaataa tatactaaca   1015 agaactata gtc aac gtt cca aaa acc aga aaa acc tac tgt aaa ggt aaa   1066
          Val Asn Val Pro Lys Thr Arg Lys Thr Tyr Cys Lys Gly Lys
                    5                  10                  15 gag tgt aga aaa cac act caa cac aaa gtt acc caa tac aaa gct ggt     1114
Glu Cys Arg Lys His Thr Gln His Lys Val Thr Gln Tyr Lys Ala Gly
             20                  25                  30 aaa gct tct tta ttt gct caa ggt aaa cgt cgt tat gac cgt aaa caa     1162
Lys Ala Ser Leu Phe Ala Gln Gly Lys Arg Arg Tyr Asp Arg Lys Gln
         35                  40                  45 tcc ggt tac ggt ggt caa acc aaa cca gtt ttc cat aaa aaa gct aaa     1210
Ser Gly Tyr Gly Gly Gln Thr Lys Pro Val Phe His Lys Lys Ala Lys
         50                  55                  60 act acc aaa aaa gtt gtt tta cgt tta gaa tgt gtt gtt tgt aaa acc     1258
Thr Thr Lys Lys Val Val Leu Arg Leu Glu Cys Val Val Cys Lys Thr
     65                  70                  75 aaa gct caa tta tca tta aaa cgt tgt aaa cat ttc gaa tta ggt ggt     1306
Lys Ala Gln Leu Ser Leu Lys Arg Cys Lys His Phe Glu Leu Gly Gly
 80                  85                  90                  95 gac aga aaa caa aaa ggt caa gct tta caa ttc taa ggt ggt              1348
Asp Arg Lys Gln Lys Gly Gln Ala Leu Gln Phe     Gly Gly
                100                 105 taaattattt gattattttg cactactatt aaaggggggt ttgtatatct taatgtaacg   1408
ttttacagat aaagattgat gtagtgggaa gtgtcctgtc tatcaaggcc tatatagact   1468
tttgactatt attttcgtag taatactacc tagatagtag atgagtctag ttgtagttcc   1528
cttcgtatgt gattcattca gcctaattaa aatcctttca aatcgccctc gcaatttta   1588 agtgtccctt cagatttgaa attagaacca aaatttctga atctgttttt gaaagggacc   1648
ataaaaagtt agtggtttca agatcaaaat caaaatcaaa atcaacttta gcgctgaatc   1708
aaatcaacaa caaccatcag tggcgttcaa cacatcacca agggcgtcaa accagggcaa   1768
aacagtacag gaaagaccac agaaacacac agaatcccata ggaaccacag gaagcaccat   1828
cacattcccc aagagcgcat tcattcccgt tgaaatcaag ctacataccc aaatagacag   1888
atcaaaacat tggaattc                                                  1906
```

<210> SEQ ID NO 2
<211> LENGTH: 106
<212> TYPE: PRT
<213> ORGANISM: Pichia ciferrii -continued

```
<400> SEQUENCE: 2

Met Val Asn Val Pro Lys Thr Arg Lys Thr Tyr Cys Lys Gly Lys Glu
  1               5                  10                  15

Cys Arg Lys His Thr Gln His Lys Val Thr Gln Tyr Lys Ala Gly Lys
             20                  25                  30

Ala Ser Leu Phe Ala Gln Gly Lys Arg Arg Tyr Asp Arg Lys Gln Ser
         35                  40                  45

Gly Tyr Gly Gly Gln Thr Lys Pro Val Phe His Lys Lys Ala Lys Thr
     50                  55                  60

Thr Lys Lys Val Val Leu Arg Leu Glu Cys Val Cys Lys Thr Lys
 65                  70                  75                  80

Ala Gln Leu Ser Leu Lys Arg Cys Lys His Phe Glu Leu Gly Gly Asp
                 85                  90                  95

Arg Lys Gln Lys Gly Gln Ala Leu Gln Phe
                100                 105

<210> SEQ ID NO 3
<211> LENGTH: 3296
<212> TYPE: DNA
<213> ORGANISM: Pichia ciferrii
<220> FEATURE:
<221> NAME/KEY: CDS
<222> LOCATION: (765)..(2453)

<400> SEQUENCE: 3
acttgatgaa taggaatggt ataaagaaaa acatgacaaa taagtaggaa gtagcagcaa      60
ctgaacctaa tgattctgga ataacaggtt tattgggttt ggataaatct ttaccatata     120
gacctatctt gatgaatgat gaagataatt ttgggattaa ataatttgtt gatatgaatc     180
caattaaact gaatcctaaa gcagcttgta atggttcagt tatcccatag gaaccttggg     240
aagtgtatat tattgttatg gctattccta ggagggatag ttctggaagg gacattgtgt     300
gattgacgta gcatgtgtaa tcaattggtg atgatattga tattgtattg atctaatagt     360
gtatagattg tttattgata tttatttgtt tacgtgtctg cttatgttat gtgttatgta     420
atacttaata ggagaattta taatagggt ataatgagaa gaataaaaga ataatgaaga     480
atatgatcaa caaagaattg aattgaatga gaataaaata ataataatat aataaaagaa     540
caataaaaga acaatataaa taataatata atcatcttat cattcaatta ccaaccactt     600
attaatcctt gcttcgttca attcttctca aacgcgaatt caaacaagaa caagtgaatt     660
tcaaatttaa acaaacaaac aaaactataa aaacaatcaa atatccagaa acagacaaac     720
caaccaacca ataccaatac caataccaat agaactatac caac atg tca ttg gta    776
                                               Met Ser Leu Val
                                                 1 ata cct caa ata gat cta tca ggt ctt tcc atc gaa gac aag aaa caa     824
Ile Pro Gln Ile Asp Leu Ser Gly Leu Ser Ile Glu Asp Lys Lys Gln
  5                  10                  15                  20 aat gaa ttc ggt gct cta act tca aat gaa tat cgt tac aaa aca att     872
Asn Glu Phe Gly Ala Leu Thr Ser Asn Glu Tyr Arg Tyr Lys Thr Ile
                 25                  30                  35 tca aga cag ggg aaa cca tta cct gat cca att gaa gat gaa cca cca     920
Ser Arg Gln Gly Lys Pro Leu Pro Asp Pro Ile Glu Asp Glu Pro Pro
             40                  45                  50 tat cat gtc ctt ttc atc act tat tta aac tat tta atc ttg att atc     968
Tyr His Val Leu Phe Ile Thr Tyr Leu Asn Tyr Leu Ile Leu Ile Ile
         55                  60                  65
```

```
                                                              -continued gtt ggt cat att aaa gat ttc aca ggt att ctg ttc aac cca aaa aat       1016
Val Gly His Ile Lys Asp Phe Thr Gly Ile Leu Phe Asn Pro Lys Asn
 70              75                  80 tac caa gat tta tta gaa caa aat ggc ctt gct cca tgg tat aat aaa       1064
Tyr Gln Asp Leu Leu Glu Gln Asn Gly Leu Ala Pro Trp Tyr Asn Lys
 85              90                  95                 100 ttt gaa agt ttt tat att cgt cgt atg aaa caa aaa att gat gat tgt       1112
Phe Glu Ser Phe Tyr Ile Arg Arg Met Lys Gln Lys Ile Asp Asp Cys
            105                 110                 115 ttt gca aga cca act tgt ggt gtc cca ggt aga tta atc act tgt att       1160
Phe Ala Arg Pro Thr Cys Gly Val Pro Gly Arg Leu Ile Thr Cys Ile
        120                 125                 130 gat cgt gat gct cat gat tat aat tca tat ttt agt tat cct ggt act       1208
Asp Arg Asp Ala His Asp Tyr Asn Ser Tyr Phe Ser Tyr Pro Gly Thr
        135                 140                 145 act tca act tgt tta aat tta tca tca tat aat tat ttg ggg ttt gca       1256
Thr Ser Thr Cys Leu Asn Leu Ser Ser Tyr Asn Tyr Leu Gly Phe Ala
    150                 155                 160 caa tct gaa ggg gca tgt act caa gcc gct tta gaa att ttg gat tat       1304
Gln Ser Glu Gly Ala Cys Thr Gln Ala Ala Leu Glu Ile Leu Asp Tyr
165                 170                 175                 180 tat ggt gtt ggt tct ggt ggt cca aga aat gtt att ggt act act gat       1352
Tyr Gly Val Gly Ser Gly Gly Pro Arg Asn Val Ile Gly Thr Thr Asp
            185                 190                 195 tta cat tta aaa act gaa aaa act ata gca aaa ttt att ggt aaa gat       1400
Leu His Leu Lys Thr Glu Lys Thr Ile Ala Lys Phe Ile Gly Lys Asp
        200                 205                 210 gat tca atc tta ttt tca atg ggg tat gca aca aat gca agt tta ttt       1448
Asp Ser Ile Leu Phe Ser Met Gly Tyr Ala Thr Asn Ala Ser Leu Phe
        215                 220                 225 agt tct tta ttg gat aag aaa tca ctt gtt att tct gat gaa tta aat       1496
Ser Ser Leu Leu Asp Lys Lys Ser Leu Val Ile Ser Asp Glu Leu Asn
    230                 235                 240 cat gct tca att aga act ggt gtt aga tta tct ggt tct aca gtt aaa       1544
His Ala Ser Ile Arg Thr Gly Val Arg Leu Ser Gly Ser Thr Val Lys
245                 250                 255                 260 act ttc cct cat aat aat atg att gcc ttg gaa aaa att ctt aga gaa       1592
Thr Phe Pro His Asn Asn Met Ile Ala Leu Glu Lys Ile Leu Arg Glu
            265                 270                 275 caa att tct caa ggt caa cca aga tct cat cgt cca tgg aaa aaa atc       1640
Gln Ile Ser Gln Gly Gln Pro Arg Ser His Arg Pro Trp Lys Lys Ile
        280                 285                 290 att gtt gca gtt gaa ggg ctt tat tca atg gag ggt aca atg gca aat       1688
Ile Val Ala Val Glu Gly Leu Tyr Ser Met Glu Gly Thr Met Ala Asn
        295                 300                 305 tta cct gca tta att gaa tta aga aga aaa tat aaa ttt aat tta ttt       1736
Leu Pro Ala Leu Ile Glu Leu Arg Arg Lys Tyr Lys Phe Asn Leu Phe
    310                 315                 320 gtt gat gaa gct cat tca att ggt gct att ggt cca tca ggt cgt ggt       1784
Val Asp Glu Ala His Ser Ile Gly Ala Ile Gly Pro Ser Gly Arg Gly
325                 330                 335                 340 gtt tgt gat tat ttt ggt ata gat ccc tca aat gtt gat tta tta atg       1832
Val Cys Asp Tyr Phe Gly Ile Asp Pro Ser Asn Val Asp Leu Leu Met
            345                 350                 355 ggg act tta act aaa tca ttt ggt gct gca ggt ggt tat att gct ggt       1880
Gly Thr Leu Thr Lys Ser Phe Gly Ala Ala Gly Gly Tyr Ile Ala Gly
        360                 365                 370 tca caa caa att ata aat cgt tta aaa tta aat att aat tca caa aat       1928
Ser Gln Gln Ile Ile Asn Arg Leu Lys Leu Asn Ile Asn Ser Gln Asn
    375                 380                 385
```

```
tat gca gaa tct atc cct gca cct gtt ttg gca caa att att tct tcg      1976
Tyr Ala Glu Ser Ile Pro Ala Pro Val Leu Ala Gln Ile Ile Ser Ser
    390                 395                 400 tta aat atc atc tcg ggt gat tta aat cct ggt gaa ggt tcg gaa aga      2024
Leu Asn Ile Ile Ser Gly Asp Leu Asn Pro Gly Glu Gly Ser Glu Arg
405                 410                 415                 420 tta gaa aga att gct ttt aat tca cgt tat tta aga tta ggt tta caa      2072
Leu Glu Arg Ile Ala Phe Asn Ser Arg Tyr Leu Arg Leu Gly Leu Gln
                425                 430                 435 aga tta ggt ttt atc gta tac gga gtt gat gat tca cca gtg atc cca      2120
Arg Leu Gly Phe Ile Val Tyr Gly Val Asp Asp Ser Pro Val Ile Pro
            440                 445                 450 tta tta tta ttc gcc cca gcc aaa atg cca gca ttt tca cgt atg cta      2168
Leu Leu Leu Phe Ala Pro Ala Lys Met Pro Ala Phe Ser Arg Met Leu
        455                 460                 465 tat caa gga aaa att tca gtt gtt gtt gtt gga tac ccg gca act cca      2216
Tyr Gln Gly Lys Ile Ser Val Val Val Val Gly Tyr Pro Ala Thr Pro
    470                 475                 480 ctg act tca tca gga gtt cgt ctt ggt gtt cct gca tct tta cca aag      2264
Leu Thr Ser Ser Gly Val Arg Leu Gly Val Pro Ala Ser Leu Pro Lys
485                 490                 495                 500 gag gat atg gat tat ctt tta cgt cat tta tcc gag ttg ggt gat aaa      2312
Glu Asp Met Asp Tyr Leu Leu Arg His Leu Ser Glu Leu Gly Asp Lys
                505                 510                 515 tta ttt tta aaa ttt agt tct ggt att gct ggt ggt tct tta gat ggt      2360
Leu Phe Leu Lys Phe Ser Ser Gly Ile Ala Gly Gly Ser Leu Asp Gly
            520                 525                 530 tca cca cca aga tgg aat att gaa gat gtt ttg aaa gag act cca aag      2408
Ser Pro Pro Arg Trp Asn Ile Glu Asp Val Leu Lys Glu Thr Pro Lys
        535                 540                 545 gat tgt aaa gaa tct aaa tat ttt att gca act gca aat aat tga          2453
Asp Cys Lys Glu Ser Lys Tyr Phe Ile Ala Thr Ala Asn Asn
    550                 555                 560 taaataattg atttataatt ttaatagcta atttaataat ttaataataa tatacaacat    2513
ctatatgatc ttttttggtg taattttatag cttatcatct tatcatctta tataatcgga   2573
atgttacaat gtaatagaaa agaatgaaaa aaaaccctta caatctgaaa aaaaagataa    2633
agatcataaa tatgcaaatt attgtttaaa atatttcttt caaacccttta ttatgatctt   2693 ttgaattcaa gtaattataa ttccttcttt cttgatcaaa ttatttccat tttttgtgta    2753
gttgatgata caaattttttc attttttgatc ttcatttttt tcaacattgc cataattttt  2813
tgaataccac caaaataaaa aataaaaaaa aaataaacac ggaaaaatta aaatcaaaac    2873
atttcaaaac attgttggtg aaaggtatac taaagatcag gttcagatat tagttattag   2933
gtattaccag gtttctcatc ataggttaag aattaggaga atacattact aggatctgat    2993
tgttgagttg ataattggtg gtagttacgt gttgctcatt tggtatagat ctcaattata    3053
cattcttttg aaaaggtgtt gataatactt tgagaatact ttgaaattat tcaaatttat    3113
agaggttcat atcattacta cattgttgat tattacaagt ttgtgtggtt ttttgaattc    3173
tcatccattc ctttatttta acactttata catatttgac atatccaatt attaccatag    3233
cattccatag catattcatc atagcatatc atattcatag caggtcattt caattatgaa    3293
ttc                                                                  3296
```

<210> SEQ ID NO 4
<211> LENGTH: 562
<212> TYPE: PRT
<213> ORGANISM: Pichia ciferrii -continued

```
<400> SEQUENCE: 4

Met Ser Leu Val Ile Pro Gln Ile Asp Leu Ser Gly Leu Ser Ile Glu
 1               5                  10                  15

Asp Lys Lys Gln Asn Glu Phe Gly Ala Leu Thr Ser Asn Glu Tyr Arg
                20                  25                  30

Tyr Lys Thr Ile Ser Arg Gln Gly Lys Pro Leu Pro Asp Pro Ile Glu
            35                  40                  45

Asp Glu Pro Pro Tyr His Val Leu Phe Ile Thr Tyr Leu Asn Tyr Leu
        50                  55                  60

Ile Leu Ile Ile Val Gly His Ile Lys Asp Phe Thr Gly Ile Leu Phe
65                  70                  75                  80

Asn Pro Lys Asn Tyr Gln Asp Leu Leu Glu Gln Asn Gly Leu Ala Pro
                85                  90                  95

Trp Tyr Asn Lys Phe Glu Ser Phe Tyr Ile Arg Arg Met Lys Gln Lys
            100                 105                 110

Ile Asp Asp Cys Phe Ala Arg Pro Thr Cys Gly Val Pro Gly Arg Leu
        115                 120                 125

Ile Thr Cys Ile Asp Arg Asp Ala His Asp Tyr Asn Ser Tyr Phe Ser
        130                 135                 140

Tyr Pro Gly Thr Thr Ser Thr Cys Leu Asn Leu Ser Ser Tyr Asn Tyr
145                 150                 155                 160

Leu Gly Phe Ala Gln Ser Glu Gly Ala Cys Thr Gln Ala Ala Leu Glu
                165                 170                 175

Ile Leu Asp Tyr Tyr Gly Val Gly Ser Gly Gly Pro Arg Asn Val Ile
            180                 185                 190

Gly Thr Thr Asp Leu His Leu Lys Thr Glu Lys Thr Ile Ala Lys Phe
        195                 200                 205

Ile Gly Lys Asp Asp Ser Ile Leu Phe Ser Met Gly Tyr Ala Thr Asn
210                 215                 220

Ala Ser Leu Phe Ser Ser Leu Leu Asp Lys Lys Ser Leu Val Ile Ser
225                 230                 235                 240

Asp Glu Leu Asn His Ala Ser Ile Arg Thr Gly Val Arg Leu Ser Gly
                245                 250                 255

Ser Thr Val Lys Thr Phe Pro His Asn Asn Met Ile Ala Leu Glu Lys
            260                 265                 270

Ile Leu Arg Glu Gln Ile Ser Gln Gly Gln Pro Arg Ser His Arg Pro
        275                 280                 285

Trp Lys Lys Ile Ile Val Ala Val Glu Gly Leu Tyr Ser Met Glu Gly
        290                 295                 300

Thr Met Ala Asn Leu Pro Ala Leu Ile Glu Leu Arg Arg Lys Tyr Lys
305                 310                 315                 320

Phe Asn Leu Phe Val Asp Glu Ala His Ser Ile Gly Ala Ile Gly Pro
                325                 330                 335

Ser Gly Arg Gly Val Cys Asp Tyr Phe Gly Ile Asp Pro Ser Asn Val
            340                 345                 350

Asp Leu Leu Met Gly Thr Leu Thr Lys Ser Phe Gly Ala Ala Gly Gly
        355                 360                 365

Tyr Ile Ala Gly Ser Gln Gln Ile Ile Asn Arg Leu Lys Leu Asn Ile
        370                 375                 380

Asn Ser Gln Asn Tyr Ala Glu Ser Ile Pro Ala Pro Val Leu Ala Gln
385                 390                 395                 400

Ile Ile Ser Ser Leu Asn Ile Ile Ser Gly Asp Leu Asn Pro Gly Glu
                405                 410                 415
```

-continued

```
Gly Ser Glu Arg Leu Glu Arg Ile Ala Phe Asn Ser Arg Tyr Leu Arg
            420                 425                 430

Leu Gly Leu Gln Arg Leu Gly Phe Ile Val Tyr Gly Val Asp Asp Ser
        435                 440                 445

Pro Val Ile Pro Leu Leu Phe Ala Pro Ala Lys Met Pro Ala Phe
    450                 455                 460

Ser Arg Met Leu Tyr Gln Gly Lys Ile Ser Val Val Val Gly Tyr
465                 470                 475                 480

Pro Ala Thr Pro Leu Thr Ser Ser Gly Val Arg Leu Gly Val Pro Ala
                485                 490                 495

Ser Leu Pro Lys Glu Asp Met Asp Tyr Leu Leu Arg His Leu Ser Glu
            500                 505                 510

Leu Gly Asp Lys Leu Phe Leu Lys Phe Ser Ser Gly Ile Ala Gly Gly
        515                 520                 525

Ser Leu Asp Gly Ser Pro Pro Arg Trp Asn Ile Glu Asp Val Leu Lys
    530                 535                 540

Glu Thr Pro Lys Asp Cys Lys Glu Ser Lys Tyr Phe Ile Ala Thr Ala
545                 550                 555                 560

Asn Asn
```

<210> SEQ ID NO 5
<211> LENGTH: 1928
<212> TYPE: DNA
<213> ORGANISM: Pichia ciferrii
<220> FEATURE:
<221> NAME/KEY: CDS
<222> LOCATION: (907)..(1911)
<221> NAME/KEY: promoter
<222> LOCATION: (1)..(906)

<400> SEQUENCE: 5

```
gttgataatt tataattgat aatgatttaa acttttgatt ataaattgat taaaacccat      60
gtcatctagt atataataac aatgaccata actataataa ttagtaccca tcaattacta     120
ataccataac atactatacc atataccata atatactata gtctatacgt ctataccata     180
tattataaca ttgtatttcc taatcaaact ttcatctgat gttttatcaa cctttgtaaa     240
ctttgatcaa ctgtttgtct gtttgtcaac tgatgattgg aaccacatga ttatatgcaa     300
agcaataaaa caacaaacaa caacaacttt acccagtggt acctacatac aattgaccca     360
tagtaaacta ataactcata acacaataaa gcatctgatc ttaatgtact actaaatact     420
aaactgatga taattacttt tgttgtaatg tttgtcatca ctttgatcat cacgagcatc     480
accggaccgt taattaccaa caatctcaat tgtacaacat agtgttaaaa caggataact     540
tgatgattat atgtgatatt aagttcaaac aagtaccaat aaatagataa ttaatagctc     600
tataatatat catttaattg aattaatatc aatagttgtt gtttaattat ccctagtttt     660
ctggttaaag ttacaccatc agatggttca ccaccaatgt tgttcaaacc atttccactc     720
aactgacgtt tccagaacat caccctgaaa aaaaaaaatt catcacacat gggagaaatt     780
tggggaggat tgtatataag gagtggaaat tcgctaatat ttttataatt ctaactcact     840
tgttttaatt caacatcagt attttataat acaaaaacaa acaaacaaac aaataattaa     900 ttaaca atg gct atc aca gtt ggt att aac ggt ttc ggt cgt att ggt     948
       Met Ala Ile Thr Val Gly Ile Asn Gly Phe Gly Arg Ile Gly
         1               5                  10 cgt tta gtc cta aga att gct ctt tca aga aaa gat att caa att gtt     996
Arg Leu Val Leu Arg Ile Ala Leu Ser Arg Lys Asp Ile Gln Ile Val
 15                  20                  25                  30
```

```
gca att aat gat cca ttc att gca cca gaa tat gct tca tat atg ttt   1044
Ala Ile Asn Asp Pro Phe Ile Ala Pro Glu Tyr Ala Ser Tyr Met Phe
            35                  40                  45 aaa tat gat tct act cat ggt cgt tat tca ggt gaa gtt tct cat gaa   1092
Lys Tyr Asp Ser Thr His Gly Arg Tyr Ser Gly Glu Val Ser His Glu
        50                  55                  60 ggt gaa aac att gtt att gat ggt aaa aaa atc aga gtt tat caa gaa   1140
Gly Glu Asn Ile Val Ile Asp Gly Lys Lys Ile Arg Val Tyr Gln Glu
        65                  70                  75 cgt gat cca gtt aat atc cca tgg ggt aaa gat ggt gtt gat tat gtt   1188
Arg Asp Pro Val Asn Ile Pro Trp Gly Lys Asp Gly Val Asp Tyr Val
 80                  85                  90 att gat tca act ggt gtt ttt aaa gaa tta gat tct gct caa aaa cat   1236
Ile Asp Ser Thr Gly Val Phe Lys Glu Leu Asp Ser Ala Gln Lys His
 95                 100                 105                 110 att gat gcc ggt gct aaa aaa gtt gtt att act gct cca tca tca act   1284
Ile Asp Ala Gly Ala Lys Lys Val Val Ile Thr Ala Pro Ser Ser Thr
                115                 120                 125 gct cca atg ttt gtt gtt ggt gtt aat gaa gat aaa tat act cca gat   1332
Ala Pro Met Phe Val Val Gly Val Asn Glu Asp Lys Tyr Thr Pro Asp
            130                 135                 140 tta aac att att tca aat gct tca tgt aca aca aat tgt tta gct cca   1380
Leu Asn Ile Ile Ser Asn Ala Ser Cys Thr Thr Asn Cys Leu Ala Pro
        145                 150                 155 tta gct aaa att att aac aat aaa ttt ggt att gaa gaa ggt tta atg   1428
Leu Ala Lys Ile Ile Asn Asn Lys Phe Gly Ile Glu Glu Gly Leu Met
160                 165                 170 act act gtt cat tca att act gct act caa aaa act gtt gat ggt cca   1476
Thr Thr Val His Ser Ile Thr Ala Thr Gln Lys Thr Val Asp Gly Pro
175                 180                 185                 190 tct cat aaa gat tgg aga agt ggt cct act gct tca ggt aat att att   1524
Ser His Lys Asp Trp Arg Ser Gly Pro Thr Ala Ser Gly Asn Ile Ile
                195                 200                 205 cca tca tca act ggt gct gct aaa gct gtt ggt aaa gtt att cca gaa   1572
Pro Ser Ser Thr Gly Ala Ala Lys Ala Val Gly Lys Val Ile Pro Glu
            210                 215                 220 ttg gct ggt aaa tta act ggt atg tct tta aga gtt cca act gtt gat   1620
Leu Ala Gly Lys Leu Thr Gly Met Ser Leu Arg Val Pro Thr Val Asp
        225                 230                 235 gtt tca gtt gtt gat tta act gtt aaa tta tta aaa gat gcc act tat   1668
Val Ser Val Val Asp Leu Thr Val Lys Leu Leu Lys Asp Ala Thr Tyr
240                 245                 250 gat gaa att aaa gct gct gtt aaa gaa gct gct gaa ggt cca tta aaa   1716
Asp Glu Ile Lys Ala Ala Val Lys Glu Ala Ala Glu Gly Pro Leu Lys
255                 260                 265                 270 ggt gtt gtt ggt tat act gaa gat caa gtt gtt tct tca gat ttc tta   1764
Gly Val Val Gly Tyr Thr Glu Asp Gln Val Val Ser Ser Asp Phe Leu
                275                 280                 285 act gat aac aga tca tca att ttt gat gct gaa gct ggt att tgg tta   1812
Thr Asp Asn Arg Ser Ser Ile Phe Asp Ala Glu Ala Gly Ile Trp Leu
            290                 295                 300 tca cca aga ttt gtt aaa tta att gct tgg tat gat aat gaa tat ggt   1860
Ser Pro Arg Phe Val Lys Leu Ile Ala Trp Tyr Asp Asn Glu Tyr Gly
        305                 310                 315 tac tct acc aga gtt gtt gat tta tta gaa tac gtt gct tca aag aac   1908
Tyr Ser Thr Arg Val Val Asp Leu Leu Glu Tyr Val Ala Ser Lys Asn
        320                 325                 330 taa gagtagaacg aaagctt                                            1928
```

```
<210> SEQ ID NO 6
<211> LENGTH: 334
<212> TYPE: PRT
<213> ORGANISM: Pichia ciferrii

<400> SEQUENCE: 6

Met Ala Ile Thr Val Gly Ile Asn Gly Phe Gly Arg Ile Gly Arg Leu
 1               5                  10                  15

Val Leu Arg Ile Ala Leu Ser Arg Lys Asp Ile Gln Ile Val Ala Ile
                20                  25                  30

Asn Asp Pro Phe Ile Ala Pro Glu Tyr Ala Ser Tyr Met Phe Lys Tyr
            35                  40                  45

Asp Ser Thr His Gly Arg Tyr Ser Gly Glu Val Ser His Glu Gly Glu
        50                  55                  60

Asn Ile Val Ile Asp Gly Lys Lys Ile Arg Val Tyr Gln Glu Arg Asp
65                  70                  75                  80

Pro Val Asn Ile Pro Trp Gly Lys Asp Gly Val Asp Tyr Val Ile Asp
                85                  90                  95

Ser Thr Gly Val Phe Lys Glu Leu Asp Ser Ala Gln Lys His Ile Asp
            100                 105                 110

Ala Gly Ala Lys Lys Val Val Ile Thr Ala Pro Ser Ser Thr Ala Pro
        115                 120                 125

Met Phe Val Val Gly Val Asn Glu Asp Lys Tyr Thr Pro Asp Leu Asn
    130                 135                 140

Ile Ile Ser Asn Ala Ser Cys Thr Thr Asn Cys Leu Ala Pro Leu Ala
145                 150                 155                 160

Lys Ile Ile Asn Asn Lys Phe Gly Ile Glu Glu Gly Leu Met Thr Thr
                165                 170                 175

Val His Ser Ile Thr Ala Thr Gln Lys Thr Val Asp Gly Pro Ser His
            180                 185                 190

Lys Asp Trp Arg Ser Gly Pro Thr Ala Ser Gly Asn Ile Ile Pro Ser
        195                 200                 205

Ser Thr Gly Ala Ala Lys Ala Val Gly Lys Val Ile Pro Glu Leu Ala
    210                 215                 220

Gly Lys Leu Thr Gly Met Ser Leu Arg Val Pro Thr Val Asp Val Ser
225                 230                 235                 240

Val Val Asp Leu Thr Val Lys Leu Leu Lys Asp Ala Thr Tyr Asp Glu
                245                 250                 255

Ile Lys Ala Ala Val Lys Glu Ala Ala Glu Gly Pro Leu Lys Gly Val
            260                 265                 270

Val Gly Tyr Thr Glu Asp Gln Val Val Ser Ser Asp Phe Leu Thr Asp
        275                 280                 285

Asn Arg Ser Ser Ile Phe Asp Ala Glu Ala Gly Ile Trp Leu Ser Pro
    290                 295                 300

Arg Phe Val Lys Leu Ile Ala Trp Tyr Asp Asn Glu Tyr Gly Tyr Ser
305                 310                 315                 320

Thr Arg Val Val Asp Leu Leu Glu Tyr Val Ala Ser Lys Asn
                325                 330

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: PCR primer
      CYH1
<221> NAME/KEY: unsure
```

```
<222> LOCATION: (15)
<223> OTHER INFORMATION: n is A, C, G, T or known base analogue
<221> NAME/KEY: unsure
<222> LOCATION: (18)
<223> OTHER INFORMATION: n is A, C, G, T or known base analogue

<400> SEQUENCE: 7
cgcgtagtta aygtnccnaa rac                                              23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: PCR primer
      CYH4
<221> NAME/KEY: unsure
<222> LOCATION: (21)
<223> OTHER INFORMATION: n is A, C, G, T or known base analogue

<400> SEQUENCE: 8
gcctggccyt tytgyttytt ntc                                              23

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: PCR primer
      No. 3 which  is used for isolation of GAPDH promoter gene

<400> SEQUENCE: 9
gatatctaca tacaattgac ccatag                                           26

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: PCR primer
      No. 4 which  is used for isolation of GAPDH promoter gene

<400> SEQUENCE: 10
ggatccttaa ttatttgttt gttt                                             24

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: PCR primer
      CH-f

<400> SEQUENCE: 11
ggtcaaacca aaccagtttt c                                                21

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: PCR primer
      CH-r
```

```
<400> SEQUENCE: 12
atggaaaact tgtttggttt gacc                                              24

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: PCR primer
      18R

<400> SEQUENCE: 13
caataattgc aatgctctat ccccagcacg                                        30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:  PCR primer
      26F

<400> SEQUENCE: 14
ggatatggat tcttcacggt aacgtaactg                                        30

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:  PCR primer
      L2f

<400> SEQUENCE: 15
atgagtactc ctgcaaacta                                                   20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: PCR primer
      L2r

<400> SEQUENCE: 16
taacaaaata cttgtcgtcc                                                   20

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: PCR primer
      No. 1 which is used for isolation of GADPH gene

<400> SEQUENCE: 17
atggttagag ttgctattaa cg                                                22

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:  PCR primer
      No. 2 which is used for isolation of GADPH gene
```

-continued

```
<400> SEQUENCE: 18
aagccttggc aatgtgttca a                                              21
```

What is claimed is:

1. An isolated L41 gene represented as SEQ ID NO: 1 and coding for a *Pichia ciferrii* ribosomal protein.

2. An expression cassette for *Pichia ciferrii* comprising:
   (a) a *Pichia ciferrii* ribosomal DNA, which is operably linked to
   (b) a modified L41 gene of SEQ ID NO: 1, wherein its encoded amino acid proline at residue 56 is replaced with glutamine, and
   (c) a desired structural gene, said modified L41 gene being operably linked to said desired structural gene.

3. The expression cassette according to claim 2, wherein said *Pichia ciferrii* ribosomal DNA is a non-transcribed region comprising the about 1.4 kb fragment of HindIII/EcoRI digestion product thereof.

4. The expression cassette according to claim 2, wherein said desired structural gene is the LCB2 gene coding for *Pichia ciferrii* serine palmitoyl transferase and represented as SEQ ID NO: 3.

5. The expression cassette according to claim 3, wherein said desired structural gene is the LCB2 gene coding for *Pichia ciferrii* serine palmitoyl transferase and represented as SEQ ID NO: 3.

6. A plasmid comprising the expression cassette according to claim 5 which is plasmid prACL2 (KCTC-0496BP) having the restriction map in FIG. 3.

7. A process for producing a protein product coded by a desired structural gene comprising the step of transforming a *Pichia ciferrii* cell with a plasmid having the expression cassette of claim 2, wherein the protein product is expressed in said *Pichia ciferrii* cell.

8. The process according to claim 7, wherein *Pichia ciferrii* is transformed by electroporation under conditions of the voltage of about 500V, the capacity of about 50 μF, and the resistance of about 800Ω.

9. A *Pichia ciferrii* cell transformed with a vector comprising the expression cassette of claim 2.

10. A *Pichia ciferrii* cell transformed with a vector comprising the expression cassette of claim 3.

11. A *Pichia ciferrii* cell transformed with a vector comprising the expression cassette of claim 4.

12. A *Pichia ciferrii* cell transformed with a vector comprising the expression cassette of claim 5.

13. A *Pichia ciferrii* cell transformed with a vector comprising the expression cassette of claim 6.

14. A process for producing tetraacetyl phytosphingosine comprising the steps of
   (a) cultivating the transformed *Pichia ciferrii* cell of claim 11 in a suitable cultivation medium; and
   (b) recovering tetraacetyl phytosphingosine therefrom.

15. A process for producing tetraacetyl phytosphingosine comprising the steps of
   (a) cultivating the transformed *Pichia ciferrii* cell of claim 12 in a suitable cultivation medium; and
   (b) recovering tetraacetyl phytosphingosine therefrom.

16. A process for producing tetraacetyl phytosphingosine comprising the steps of
   (a) cultivating the transformed *Pichia ciferrii* cell of claim 13 in a suitable cultivation medium; and
   (b) recovering tetraacetyl phytosphingosine therefrom.

17. An isolated LCB2 gene represented as SEQ ID NO: 3 and coding for *Pichia ciferrii* serine palmitoyl transferase.

18. An expression cassette for *Pichia ciferrii* comprising:
   (a) a *Pichia ciferrii* ribosomal DNA, which is operably linked to
   (b) a modified L41 gene encoding for the polypeptide consisting of amino acid residues of SEQ ID NO: 2, wherein its encoded amino acid proline at residue 56 is replaced with glutamine, and
   (c) a desired structural gene, said modified L41 gene being operably linked to said desired structural gene.

* * * * *